United States Patent [19]

Flavin et al.

[11] Patent Number: 6,043,271

[45] Date of Patent: Mar. 28, 2000

[54] METHOD FOR THE PREPARATION OF (±)-CALANOLIDE A AND INTERMEDIATES THEREOF

[75] Inventors: Michael T. Flavin, Darien; Ze-Qi Xu, Naperville; John D. Rizzo, Downers Grove; Alla Kucherenko, Naperville; Albert Khilevich, Glenview; Abram Kivovich Sheinkman, Naperville; Vilayphone Vilaychack, Elgin; Lin Lin, Chicago; Wei Chen, Naperville, all of Ill.; William A. Boulanger, Schenectady, N.Y.

[73] Assignee: Sarawak MediChem Pharmaceuticals, Inc., Lemont, Ill.

[21] Appl. No.: 08/510,213

[22] Filed: Aug. 2, 1995

Related U.S. Application Data

[63] Continuation-in-part of application No. 08/285,655, Aug. 3, 1994, Pat. No. 5,489,697.
[51] Int. Cl.[7] .......................... A61K 31/35; C07D 407/00
[52] U.S. Cl. .......................... 514/453; 549/277; 549/278; 549/282
[58] Field of Search ................................... 549/278, 277, 549/282; 514/453

[56] References Cited

FOREIGN PATENT DOCUMENTS

92/06695   4/1992   WIPO .
93/20082  10/1993   WIPO .
94/14789   7/1994   WIPO .
94/28000  12/1994   WIPO .

OTHER PUBLICATIONS

Palmer et al. (1994), "Synthesis of the *Calophyllum* coumarins," *Tet. Letters*, vol. 35, pp. 5363–5366.

Kashman et al. (1992), "The Calanolides, a Novel HIV–Inhibitory Class of Coumarin Derivatives from the Tropical Rainforest Tree, *Calophyllum lanigerum*," *J. Med. Chem.*, vol. 35, pp. 2735–2743.

Crombie et al. (1985), Synthesis of Mammeins and Surangin A, *Tet. Letters*, vol. 26, pp. 2929–2932.

Games et al. (1972), "Identification of 4–Phenyl and 4–Alkycoumarins in Mammea Americana L., Mammea Africana G. Don and Calophyllum Inophyllum by Gas Chromatography–Mass Spectrometry," *Tet. Letters*, vol. 31, pp. 3187–3190.

Crombie et al. (1966), "Isolation and Structure of Mammea B/BA, B/BB, B/BC and C/BB: A Group of 4–m–Propyl– and 4–n–Amyl–Coumarin Extractives of Mammea Americana L.," *Tet. Letters*, vol. 2, pp. 151–156.

Cooper et al. (1994), GR15987 and Related Analogues as Highly Potent, Orally Active Non–Peptide Neurokinin $NK_2$ Receptor Antagonists, *Bioorganic & Med. Chem. Lett.*, vol. 4, pp. 1951–1956.

Hizi et al. (1993), "Specific Inhibition of the Reverse Transcriptase of Human Immunodeficiency Virus Type 1 and the Chimeric Enzymes of Human Immunodeficiency Virus Type 1 and Type 2 by Nonnuceloside Inhibitors," *Antimicrobial Agents and Chemotherapy*, vol. 37, pp. 1037–1042.

Buckheit et al. (1995), "Comparative Anti–HIV Evaluation of Diverse HIV–1–Specific Reverse Transcriptase Inhibitor––Resistant Virus Isolates Demonstrates the Existence of Distinct Phenotypic Subgroups," *Antiviral Research*, vol. 26, pp. 117–132.

Buckheit et al. (1995), "Resistance to 1–[(2–Hydroxyethoxy)methyl]–6–(phenylthio)thymine Derivatives is Generated by Mutations at Multiple Sites in the HIV–1 Reverse Transcriptase," *Virology*, vol. 210, pp. 186–193.

Bandara et al. (1986), "Two Chemically Distinct Groups of Calophyllum Species From Sri Lanka," *Phytochemistry*, vol. 25, pp. 425–428.

Boyd, M., "AIDS: Etiology, Diagnosis Treatment and Prevention," Chapter 18, 2nd Ed., J.B. Lippincott Co., Devita et al., ed., pp. 305–317.

Chaturvidi et al. (1974), "Anticonvulsant and Antinflammatory Activity of Natural Plant Coumarins and Triterpenoids," *Res. Communications in Chemical Pathology and Pharmacology*, vol. 9, pp. 11–22.

Craig et al. (1991), "Antiviral Properties of Ro 31–8959, An Inhibitor of Human Immunodeficiency Virus (HIV) Proteinase," *Antiviral Research*, vol. 16, pp. 295–305.

Dahanayake et al. (1974), "Chemical Investigation of Ceylonese Plants. Part VII. Extractives of *Calophyllum thwaitesii* Planch and Triana and *Calophyllum walkeri* Wight (Guttiferae)," *J.C.S. Perkin I*, pp. 2510–2514.

Dharmaratne et al. (1985), "Triterpenoids and Coumarins from the Leaves of *Calophyllum cordatao–oblonqum*," *Phytochemistry*, vol. 24, pp. 1553–1556.

Dharmaratne et al. (1986), "Xanthones from Roots of Three Calophyllum Species,"*Phytochemistry*, vol. 25, pp. 1957–1959.

Gautier et al. (1972), "Structure of Calophynic Acid, A Novel Constituent of *Calophyllum inophyllum*," *Tetrahedron Letters*, vol. 27, pp. 2715–2718.

(List continued on next page.)

*Primary Examiner*—Amelia Owens
*Attorney, Agent, or Firm*—McDonnell, Boehnen, Hulbert & Berghoff

[57] ABSTRACT

A method of preparing (±)-calanolide A, 1, a potent HIV reverse transcriptase inhibitor, from chromene 4 is provided. Useful intermediates for preparing (±)-calanolide A and its derivatives are also provided. According to the disclosed method, chromene 4 intermediate was reacted with acetaldehyde diethyl acetal or paraldehyde in the presence of an acid catalyst with heating, or a two-step reaction including an aldol reaction with acetaldehyde and cyclization either under acidic conditions or neutral Mitsunobu conditions, to produce chromanone 7. Reduction of chromanone 7 with sodium borohydride, in the presence of cerium trichloride, produced (±)-calanolide A. A method for resolving (±)-calanolide A into its optically active forms by a chiral HPLC system or by enzymatic acylation and hydrolysis is also disclosed. Finally, a method for treating or preventing a viral infections using (±)-calanolide or (–)-calanolide is provided.

12 Claims, 24 Drawing Sheets

OTHER PUBLICATIONS

Gunasekera et al. (1977), "Chemical Investigation of Ceylonese Plants. Part 27. Extractives of *Calophyllum cuneifolium* Thw. and *Calophyllum soulattri* Burm. F. (Guttiferae)," *J.C.S. Perkin I*, pp. 1505–1511.

Gunasekera et al. (1975), "Chemical Investigation of Ceylonese Plants. Part XVI. Extractives of *Calophyllum cardato–oblonqum* Thw. (Guttiferae)," *J.C.S. Perkin I*, pp. 2215–2220.

Gunatilaka et al. (1984), "Terpenoid and Biflavanoid Constituents of *Calophyllum calaba* and *Garcinia spicata* From Sri Lanka," *Phytochemistry*, vol. 23, pp. 323–328.

Gustafson et al. (1992), "A Nonpromoting Phorbol from the Samoan Medicinal Plant *Homalanthus nutans* Inhibits Cell Killing by HIV–1," *J. Med. Chem.*, vol. 35, pp. 1978–1986.

Gustafson et al. (1992), "AIDS–Antiviral Natural Products Research at the U.S. National Cancer Institute," in *Natural Products as Antiviral Agents*, Chu et al., eds. Plenum Press, New York, 1992, pp. 57–67.

Kawazu et al. (1972), "Piscicidal Constituents of *Capophyllum inophyllum*," *Chemical Abstracts*, vol. 78, Abstract No. 13744F.

Kumar et al. (1982), "Calocalabaxanthone, The Putative Isoprenyl Precursor of Calabaxanthone From *Calophyllum calaba*," *Phytochemistry*, vol. 21, pp. 807–809.

Merigan et al. (1991), "Treatment of AIDS with Combinations of Antiretroviral Agents," *Am. J. of Medicine*, vol. 90, pp. 8S–17S.

McCaffrey et al. (1988), "A Rapid Fluorometric DNA Assay for the Measurement of Cell Density and Proliferation In Vitro," *In Vitro Cellular & Developmental Biology*, vol. 24, Part I, pp. 247–252.

Ohtani et al. (1991), "A New Aspect of the High–Field of NMR Application of Mosher's Method. The Absolute Confirugation of Marine Triterpene Sipholenol–A," *J. Org. Chem.*, vol. 56, pp. 1296–1298.

Ohtani et al. (1989), "Absolute Configuration of Marine Diterpenes Possessing a Xenicane Skelton. An Application of an Advanced Mosher's Method," *Tetrahedron Letters*, vol. 30, pp. 3147–3150.

Pauwels et al. (1992), "Potent and Selective Inhibition of HIV–1 Replication In Vitro by a Novel Series of TIP Derivatives," *Nature*, vol. 343, pp. 470–474.

Rink et al. (1982), "Cytoplasmic pH and Free $Mg^{2+}$ in Lymphocytes," *J. of Cell Biology*, vol. 95, pp. 189–196.

Samaraweera et al. (1981), "Calozeylanic Acid, A New Bark Acid From Three Calophyllum Species," *Tetrahedron Letters*, vol. 22, pp. 5083–5086.

Saunders et al. (1992), "Non–nucleoside Inhibitors of HIV reverse Transcriptase," *Drug Design and Discovery*, vol. 8, pp. 255–263.

Shih et al. (1991), "Chimeric Human Immunodeficiency Virus Type 1/Type 2 Reverse Transcriptases Display Reversed Sensitivity to Nonnucleoside Analog Inhibitors," *Proc. Natl. Acad. Sci. USA*, vol. 88, pp. 9878–9982.

Stout et al. (1968), "Calophyllum Products III. The Structures of Blancoic Acids," *J. Organic Chemistry*, vol. 33, pp. 4185–4190.

Stout et al. (1964), "The Structure of Costatolide," *J. Organic Chemistry*, vol. 29, pp. 3604–3609.

Swagler et al. (1991), "Pharmacokinetics of Anti–HIV Nucleosides in Microswine," *J. Pharm. Pharmacol.*, vol. 43, pp. 823–826.

Soejarto et al. (1993), "Challenges in Developing a New Drug from Tropical Rain Forest Plants," In *Proceedings of the Symposium on the Industrial Utilization of Tropical Plants and the Conservation of Biodiversity*, Enugu, Nigeria, Feb. 14–19, 1993.

Somanathan et al. (1974), "Chemical Investigation of Ceylonese Plants. Part VIII. Trapezifolixanthone, a New Di–isoprenylated Xanthone from the Bark of *Calophyllum trapezifolium* Thw. (Guttiferae)," *J.C.S. Perkin I*, pp. 2515–2517.

White et al. (1991), "A TIBO Derivative, R82913, Is A Potent Inhibitor of HIV–1 Reverse Transcriptase with Heteropolymer Templates," *Antiviral Research*, vol. 16, pp. 257–266.

Boyer et al. (1993), "Analysis of Nonnucleoside Drug–Resistant Variants of Human Immunodeficiency Virus Type 1 Reverse Transcriptase," *J. Virology*, vol. 67, pp. 2412–2420.

McKee et al. (1995), "The Pseudocalanolides: Structure Revision of Calanolides C and D," *J. Natural Produts*, vol. 58, pp. 916–920.

Kucherenko et al. (1995), "Novel Approach for Synthesis of (±)–Calanolide A and Its Anti–HIV Activity," *Tet. Letters*, vol. 36, pp. 5475–5478.

Gustafson et al. (1994), "Calanone, a Novel Coumarin From *Calophyllum teysmannii*," *Tet. Letters*, vol. 35, pp. 5821–5824.

Kashman et al. (1993), "The Calanolides, a Novel HIV–Inhibitory Class of Coumarin Derivatives from the Tropical Rainforest Tree, *Calophyllum lanigerum*," *J. Med. Chem.*, vol. 36, pp. 1110.

Bader et al. (1991), "Oxathiin Carboxanilide, a Potent Inhibitor of Human Immunodificiency Virus Reproduction," *Proc. Natl. Acad. Sci. USA*, vol. 88, pp. 6740–6744.

Borch et al. (1971), "The Cyanohydridoborate Anion as a Selective Reducing Agent," *J. Amer. Chem. Soc.*, vol. 93, pp. 2897–2904.

Buckheit et al. (1994), "Cell–Based and Biochemical Analysis of the Anti–HIV Activity of Combination of 3'–Azido–3'–Deoxythymidine and Analogues of TIBO," *Antiviral Chemistry & Chemotherapy*, vol. 5(1), pp. 35–42.

Castro, B.R. (1983), "Replacement of Alcoholic Hydroxyl Groups by Halogens and Other Nucleophiles via Oxyphosphonium Intermediates," *Org. React.*, vol. 29, pp. 1–162.

Cooper et al. (1994), GR15987 and Related Analogues as Highly Potent, Orally Active Non–Peptide Neurokinin NK, Receptor Antagonists, *Bioorganic & Med. Chem. Lett.*, vol. 4, 1951–1956.

Feuer et al. (1965), "The Reduction of Oximes with Diborane. A New Synthesis of N–Monosubstituted Hydroxylamines," *J. Org. Chem.*, vol. 30, pp. 2877–2880.

Feuer and Braunstein (1969), "The Reduction of Oximes, Oxime Ethers, and Oxime Esters with Diborane. A Novel Synthesis of Amines," *J. Org. Chem.*, vol. 34, pp. 1817–1821.

Hudlicky, M. (1988), "Fluorination with Diethylaminosulfur Trifluoride and Related Aminofluorosulfuranes," *Org. React.*, vol. 35, pp. 513–637.

Hughes, D.L. (1992), "The Mitsunobu Reaction," *Organic Reaction*, vol. 42, pp. 335–656.

Kukla et al. (1991), "Synthesis and Anti–HIV–1 Activity of 4,5,6,7–Tetrahydro–5–methylimidazo[4,5,1–jk][1,4] benzodiazepin–2(1H)–one (TIBO) Derivatives," *J. Medicinal Chemistry*, vol. 34, pp. 746–751.

Lin et al. (1994), "Synthesis and Biological Evaluation of 2',3'–Dideoxy–L–pyrimidine Nucleosides as Potential Antiviral Agents Against Human Immunodeficiency Virus (HIV) and Hepatitis B Virus (HBV)," *J. Med. Chem.*, vol. 37, pp. 798–803.

Massa et al. (1995), "Synthesis and Antiviral Activity of New 3,4–dihydro–2–alkoxy–6–benzyl–4–oxopyrimidines (DABOs), Specific Inhibitors of Human Immunodeficiency Virus Type 1," *Antiviral Chemistry and Chemotherapy*, vol. 6, pp. 1–8.

Mayaux et al. (1994), "Triterpene Derivatives that Block Entry of Human Immunodeficiency Virus Type 1 Into Cells," *Proc. Natl. Sci. USA*, vol. 91, pp. 3564–3568.

McGuigan et al. (1994), "Synthesis and Anti–HIV Activity of Some Novel Diaryl Phosphate Derivatives of AZT," *Antiviral Research*, vol. 24, pp. 69–77.

McMahon et al. (1993), "Diarylsulfones, a New Chemical Class of Nucleoside Antiviral Inhibitors of Human Immunodeficiency Virus Type 1 Reverse Transcriptase," *Antimicrobial Agents and Chemotherapy*, vol. 37, pp. 754–760.

Meier et al. (1992), "O–Alkyl–5',5'–dinucleoside Phosphates as Prodrugs of 3'–Azidothymidine and Cordycepin," *J. Org. Chem.*, vol. 57, pp. 7300–7308.

Merluzzi et al. (1990), "Inhibition of HIV–1 Replication by a Nucleoside Reverse Transcriptase Inhibitor," *Science*, vol. 250, pp. 1411–1413.

Mitsunobu, O. (1981), "The Use of Diethyl Azodicarboxylate and Triphenylphosphine in Synthesis and Transformation of Natural Products," *Synthesis*, pp. 1–28.

Miyasaka et al. (1989), "A Novel Lead for Specific Anti––HIV–1 Agents: 1–[(2–Hydroxyethoxy)methyl]–6–(phenylthio)–thymine," *J. Medicinal Chemistry*, vol. 32, pp. 2507–2509.

Nielson and Houlihan (1968), "The Aldol Condensation," *Org. React.*, vol. 16, pp. 1–438.

Pauwels et al. (1990), "Potent and Selective Inhibition of HIV–1 Replication In Vitro by a Novel Series of T180 Derivatives," *Nature*, vol. 343, pp. 470–474.

Pauwels et al. (1988), "Rapid and Automated Tetrazolium––Based Colorimetric Assay for the Detection of Anti–HIV Compounds," *J. Virological Methoods*, vol. 309–321.

Sergheraert et al. (1993), Synthesis and Anti–HIV Evaluation of D4T and D4T 5'–Monophosphate Prodrugs, *J. Medicinal Chemistry*, vol. 36, pp. 826–830.

Wasserman et al. (1989), "The Chemistry of Vicinal Tricarbonyls, Use of Vinyl Tricarbonyl Esters in the Formation of 3–Hydroxypyrrole–2–Carboxylates," *Tet. Letters*, vol. 30, pp. 1721–1724.

Khilevich et al., (1996) *Chemical Abstracts*, vol. 125, No. 21, Abstract No. 275454.

Khilevich et al., (1996) "Synthesis of (+)–Calanolide A. and anti–HIV agents, via enzyme catalyzed resolution of the aldol products." *Tetrahedron Asymmetry*, vol. 7, No. 11, pp. 3315–3326.

Palmer et al., (1995) "Synthesis of the Calophyllum Coumarines. Part 2.", *Journal Of The Chemical Society*, Perkin Trans. I, pp. 3135–3152.

Rehder et al., (1996), *Chemical Abstracts*, vol. 125, No. 23, Abstract No. 300646.

Galinis et al., (1996) "Structre–activity modifications of the HIV inhibitors (+)–Calanolide A and (–) Calanolide B.", *Journal of Medicinal Chemistry*, vol. 39, pp. 4507–4510.

Zembower et al., (1997) "Structural Analogues of the Calanolide Anti–HIV Agents. Modification of the Trans–10, 11–dimethyldihydropyran–12–ol Ring (Ring C)." *Journal of Medicinal Chemistry*, vol. 40, No. 6, pp. 1005–1017.

Brookmeyer, R. (1991), *Science*, vol. 253, pp. 37–42.

Braun et al. (1990), *Annu. Rev. Microbiol.*, vol. 44, pp. 555–577.

Weislow et al. (1989), *J. Natl. Cancer Inst.*, vol. 81, 577–586.

Mitsuya et al. (1990), *Science*, vol. 249, pp. 1533–1544.

Petteway et al. (1991), *Trends Pharmacol. Sci.*, vol. 12, pp. 28–34.

Richman, D.D. (1991), *Annu. Rev. Med.*, vol. 42, pp. 69–90.

Hadden, J.W. (1991), *Trends Pharmacol. Sci.*, vol. 12, pp. 107–111.

Huff, J.R. (1991), *J. Med. Chem.*, vol. 34, pp. 2305–2314.

De Clercq, E. (1992), *AIDS Research and Human Retroviruses*, vol. 8, pp. 119–134.

Kashman et al. (1992), *J. Med. Chem.*, vol. 35, pp. 2735–2743.

Chenera et al. (1993), *J. Org. Chem.*, vol. 58, pp. 5605–5606.

Sethna et al. (1953), *Organic Reactions*, Chapter 1, pp. 1–58.

Crombie et al. (1987), *Chem. Soc.*, vol. 1, pp. 317–330.

Széll et al. (1969), *Helvetica Chimica Acta*, vol. 52, pp. 2636–2641.

Barton et al. (1990), *Tetrahedron Letters*, vol. 31, pp. 7449–7452.

Fung et al. (1978), *J. Org. Chem.*, vol. 43, pp. 3977–3979.

Gemal et al. (1981), *J. Am. Chem. Soc.*, vol. 103, pp. 5454–5459.

Rao et al. (1994), *Tetrahedron Letters*, vol. 35, pp. 6347–6350.

Cardellina et al. (1995), *Bioorg. Med. Chem. Lett.* vol. 5, pp. 1011–1014.

Deshpande et al. (1995), *J. Org. Chem.*, vol. 60, pp. 2964–2965.

Mukaiyama, T. (1982), *Org. React.*, vol. 28, pp. 203–331.

Reetz et al. (1984), *Angew. Chem. Int. Ed. Eng.*, vol. 23, pp. 556–569.

Shibeta and Baba (1994), *Org. Prep. Proc. Int.* vol. 26, pp. 85–100.

Duthaler et al. (1992), *Chem. Rev.*, vol. 92, pp. 807–832.

Paterson et al. (1989), *Tetrahedron Lett.*, vol. 30, pp. 7121–7124.

Tsunoda et al. (1995), *Tetrahedron Lett.*, vol. 36, pp. 2529–2530.

Gulakowski et al. (1991), *J. Virol. Methods*, vol. 33, pp. 87–100.

Larder et al. (1989), *Science*, vol. 243, pp. 1731–1734.

Nunberg et al. (1991), *J. Virol.*, vol. 65, pp. 4887–4892.

Cragg et al. (1993), Conservation of Biodiversity and the Potetntial for Development of Pharmaceutical Crops: Drug Discovery and Development at the United States National Cancer Institute, In *Proceedings of the Symposium on the Industrial Utilization of Tropical Plants and the Conservation of Biodiversity*, Enugu, Nigeria, Feb. 14–19.

Hertzberg et al. (1993), "Kinetic Studies of HIV–1 Reverse Transcriptase Inhibition by Inophyllums, A Novel Class of Non–Nucleoside Inhibitors, Using a Scintillation Proximity Assay," *Programs and Abstracts of the Third International Conference on the Biotechnology of Microbial Products: Novel Pharmacological and Agrobiological Activities*, P–42, 27, Apr. 1993.

Hertzberg et al. (1993), "Novel Methods for Antiviral Drug Discovery," *Programs and Abstracts of the Third International Conference on the Biotechnology of Microbial Products: Novel Pharmacological and Agrobiological Activities*, S–9, 17, Apr. 1993.

Mabberley, D.J. (1987), *The Plant Book*, Cambridge University Press, p. 92.

Patil et al. (1993), "The Inophyllums, Novel Inhibitors of HIV–1 Reverse Transcriptase," *Programs and Abstracts of the Third International Conference on the Biotechnology of Microbial Products: Novel Pharmacological and Agrobiological Activities*, P–31, 26, Apr. 1993.

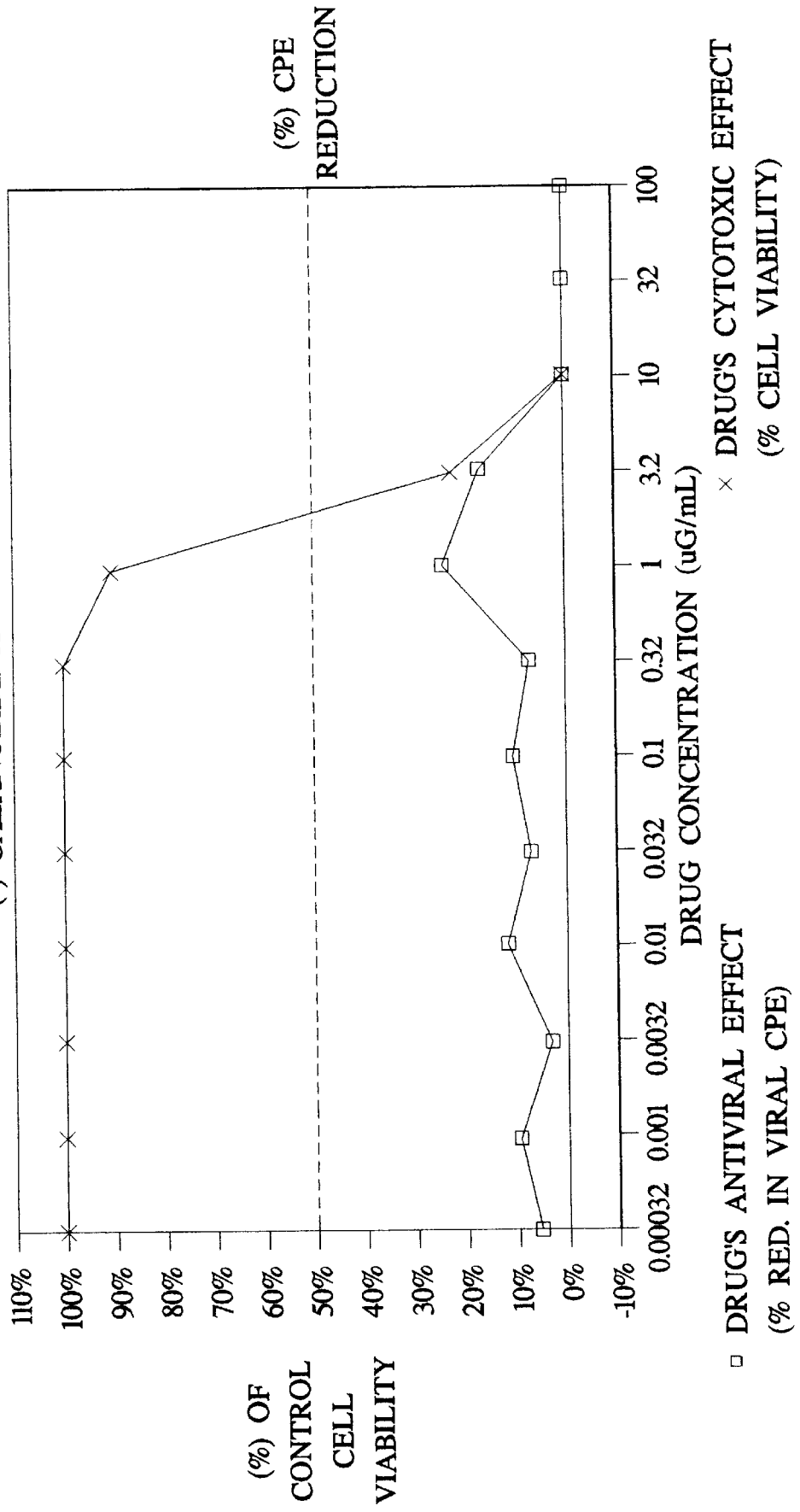

METHOD FOR THE PREPARATION OF (±)-CALANOLIDE A AND INTERMEDIATES THEREOF

CROSS REFERENCE

This is a continuation-in-part of U.S. patent application Ser. No. 08/285,655, filed Aug. 3, 1994, now U.S. Pat. No. 5,489,697, issued Feb. 6, 1996.

FIELD OF THE INVENTION

This invention relates to a method for the preparation of (±)-calanolide A, a potent inhibitor of HIV reverse transcriptase, and intermediates thereof. In particular, this invention relates to a method for large scale production of (±)-calanolide A, chiral resolution of (±)-calanolide A into its optically active forms, and use of (±)-calanolide A and (–)-calanolide for treating viral infections.

BACKGROUND OF THE INVENTION

Human immunodeficiency virus (HIV), which is also called human T-lymphotropic virus III (HTLV-III), lymphadenopathy-associated virus (LAV) or AIDS-associated retrovirus (ARV), was first isolated in 1982 and has been identified as the etiologic agent of the acquired immunodeficiency syndrome (AIDS) and related diseases. Since then, chemotherapy of AIDS has been one of the most challenging scientific endeavors. So far, AZT, ddC, ddI, and D4T have been approved by FDA and are being clinically used as drugs for the treatment of AIDS and AIDS-related complex. Although these FDA-approved drugs can extend the life of AIDS patients and improve their quality of life, none of these drugs are capable of curing the disease. Bone-marrow toxicity and other side effects as well as the emergence of drug-resistant viral strains limit the long-term use of these agents.[1] On the other hand, the number of AIDS patients wordwide has increased dramatically withing the past decade and estimates of the reported cases in the very near future also continue to rise dramaticlly. It is therefore apparent that there is a great need for other promising drugs having improved selectivity and activity to combat AIDS.[1] Several approaches including chemical synthesis, natural products screening, and biotechnology have been utilized to identify compounds targeting different stages of HIV replication for therapeutic intervention.[2]

Very recently, the screening program at the National Cancer Institute has discovered a class of remarkabley effective anti-HIV natural products, named calanolides, from the rain forest tree *Calophyllunm lanigerum*, with calanolide A, 1, being the most potent compound in the reported series.[3] For example, calanolide A demonstrated 100% protection against the cytopathic effects of HIV-1, one of two distinct types of HIV, down to a concentration of 0.1 $\mu$M. This agent also halted HIV-1 replication in human T-lymphoblastic cells (CEM-SS) ($EC_{50}$=0.1 $\mu$M/$IC_{50}$=20 $\mu$M).[3] More interestingly and importantly, calanolide A was found to be active against both the AZT-resistant G-9106 strain of HIV as well as the pyridinone-resistant A17 virus.[3] Thus, the calanolides, known as HIV-1 specific reverse transcriptase inhibitors, represent novel anti-HIV chemotherapeutic agents for drug development.

A natural source of calanolide A is limited.[4] Consequently, a practical synthesis of the natural product must be developed for further study and development to be carried out on this active and promising series of compounds. Herein, we describe a method for the synthesis and resolution of (±)-calanolide A and some related compounds.

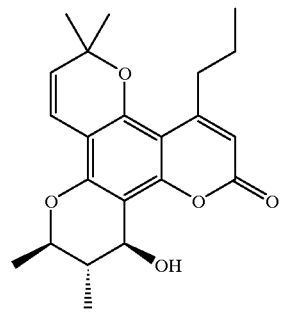

1

OBJECTS OF THE INVENTION

Accordingly, one object of the present invention is to provide a simple and practical method for preparing (±)-calanolide A, 1, from readily available starting materials and resolving the same into its optically active forms via a chiral HPLC system or enzymatic acylation and hydrolysis.

Another object of the invention is to provide useful intermediates for preparing derivatives of (±)-calanolide A.

A further object of the invention is to provide a simple and practical method for large scale preparation of (±)-calanolide A in high yields from key intermediate chromene 4.

An additional object of the invention is to provide a method for treating or preventing viral infections using (±)-calanolide A and (–)-calanolide A.

These and other objects of the invention will become apparent in view of the detailed description below.

SUMMARY OF THE INVENTION

The present invention relates to the syntheses of (±)-calanolide A and intermediates thereof, chiral resolution of (±)-calanolide and method of treating or preventing viral infections using (±)- and (–)-calanolide A.

The method of the present invention for preparing (±)-calanolide A, 1, employs chromene 4 as the key intermediate. Chromene 4 is synthesized by the sequence depicted in Scheme I. Thus, 5,7-dihydroxy-4-propylcoumarin, 2,[5] was prepared quantitatively from ethyl butyrylacetate and phloroglucinol under Pechmann conditions.[6] Product yield and purity were dependent on the amount of sulfuric acid used. The 8-position of 5,7-dihydroxy-4-propycloumarin, 2, was then selectively acylated at 8–10° C. by propionyl chyloride and $AlCl_3$ in a mixture of carbon disulfide and nitrobenzene to afford 5,7-dihydroxy-8-propionyl-4-propylcoumarin, 3.

In an alternative and preferred reaction, coumarin intermediate 3 can be produced in large scale quantities and with minimal formation of undesirable 6-position acyated product and 6,8-bis-acylated product by selective acylation of 5,7-dihydroxy-4-propylcoumarin 2 with a mixture of propionic anhydride and $AlCl_3$ at about 70–75° C.

The chromene ring was introduced upon treatment of compound 3 with 4,4-dimethoxy-2-methylbutan-2-ol,[8] providing 4 in 78% yield (Scheme I).

As presented in Scheme II, Robinson-Kostanecki reaction[9] on 4 by using sodium acetate in refluxing acetic anhydride produced enone 5 in a 65% yield. This intermediate failed to afford calanolide A upon reduction with borohydride reagents such as $NaBH_4CeCl_3$, $NaBH_4/CuCl_2$, L-selectride, 9-BBN, and DIP-chloride, and some transition metal reducing agents such as $SmI_2$ and $[(Ph_3P)\ CuH]_6$, presumably because attack at the pyrone and ring opening occurred preferentially. Treatment of 5 with Baker's yeast also resulted in coumarin ring cleavage while tri-n-butyltin hydride[10] led to reduction of 5 to enol 6 in modest yield. However, treatment of 4 with acetaldehyde diethyl acetal in the presence of trifluoroacetic acid and pyriding with heating at 160° C. produced chromanone 7 which can then be reduced into the final product.

SCHEME I

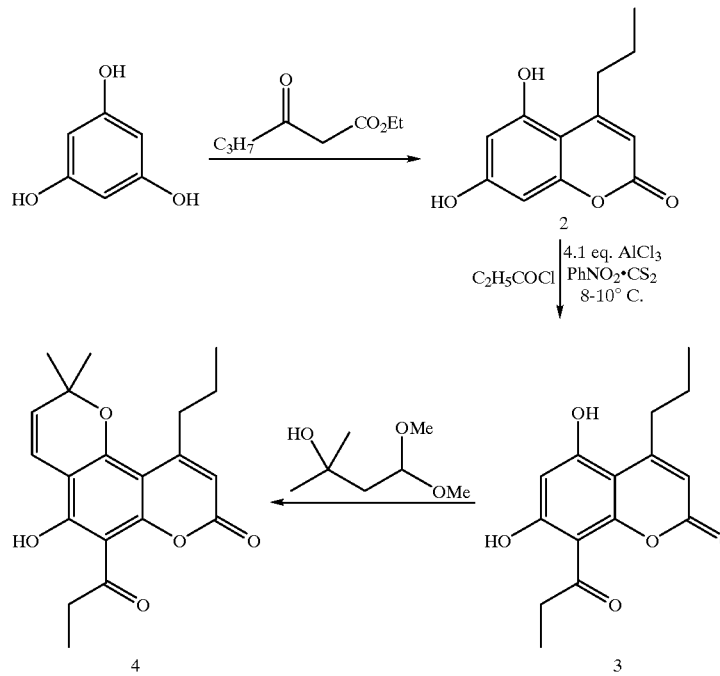

SCHEME II

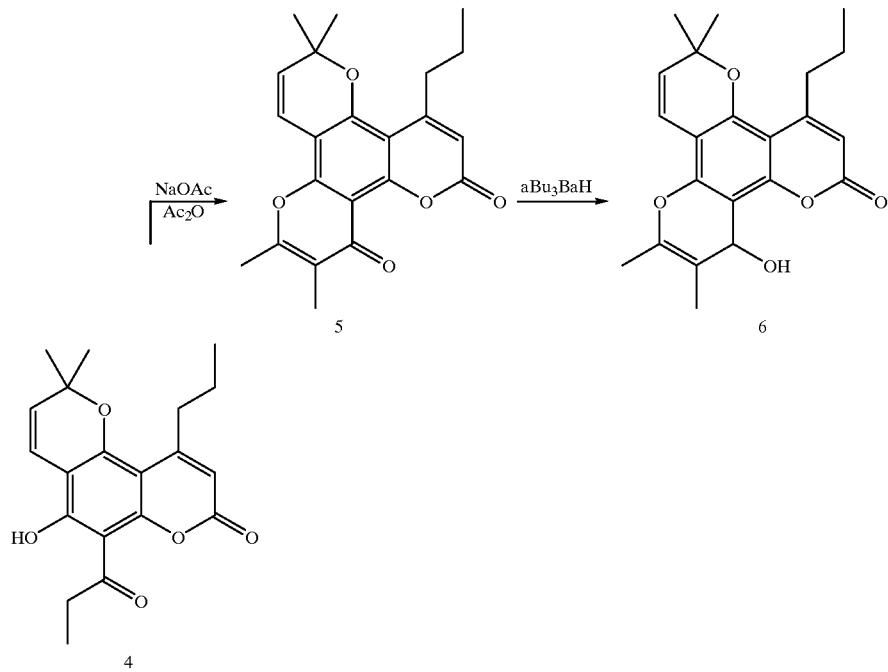

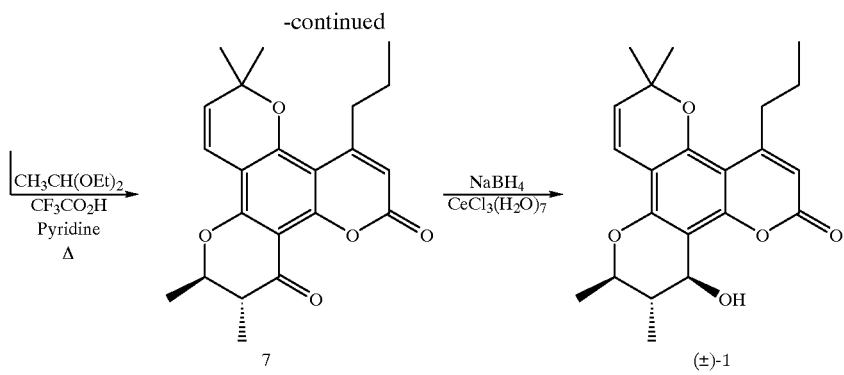

Large scale production of chromanone 7 from chromene 4 can be effected under two different reactions conditions. In a one-step reaction, chromene 4 is treated with paraldehyde, instead of acetaldehyde diathylacetal, and cylized in the presence of an acid catalyst to afford chromanone 7 in 27% yield along with 8% of the corresponding 10,11-cis-dimethyl derivative 7a. In a two-step reaction under aldol condensation conditions, chromene 4 was reacted with acetaldehyde to form an open-chain aldol product 7b. Aldol product 7b was then cyclized under acidic conditions such as 50% $H_2SO_4$ TsOH to form both chromanone 7 and 10,11-cis-dimethyl derivative 7a in a 1:1 ratio with the former leading to 16% purified yield. However, under neutral Mitsunobu[11] conditions, 7b was reproducibly cyclized to give chromanone 7 as the predominant product and in 48% yield.

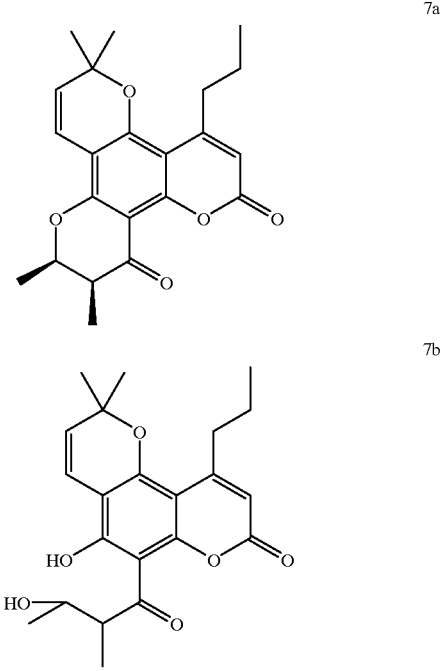

Finally, (±)-calanolide A was successfully formed with the desired stereochemical arrangement by subjecting chromanone 7 to Luche reduction[12] conditions (see Scheme II). (±)-Calanolide A was then resolved into optically active forms using a preparative HPLC chiral separating system[3].

DESCRIPTION OF THE DRAWINGS

FIGS. 2(a) to 2(e) illustrate in vitro MTT assay results, as described in Example 15, using H112-2 HIV viral strain which was not pre-treated with AZT.

DETAILED DESCRIPTION OF THE INVENTION

Figure 1A:
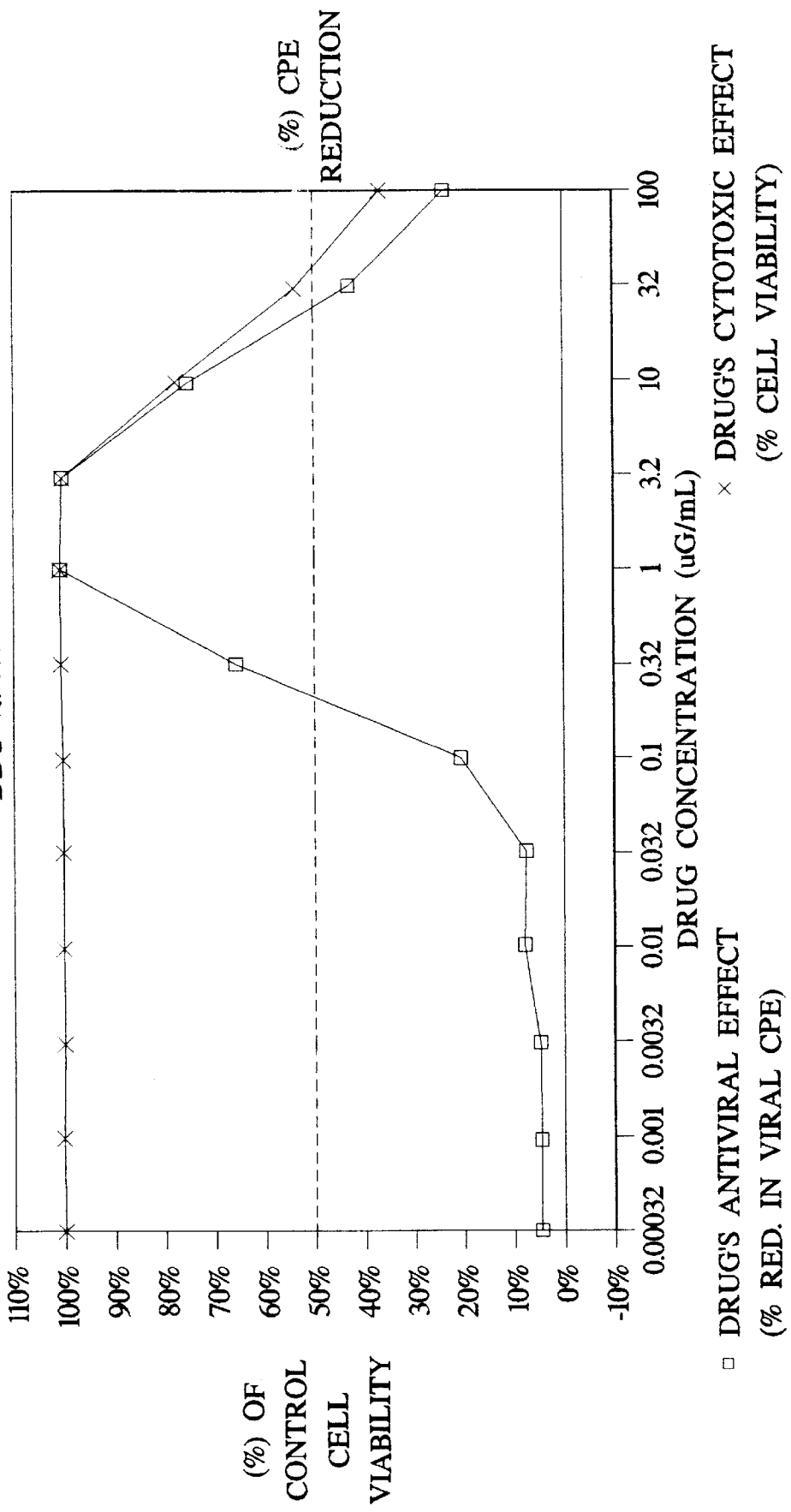
FIGS. 1(a) to 1(e) illustrate in vitro MTT assay results, as described in Example 15, using G9106 HIV viral strain which is AZT-resistant.

All patents, patent applications, and literature references cited herein are incorporated by reference in their entirety.

According to the method of the present invention, chromene 4 is a key intermediate in the preparation of (±)-calanolide A, 1. A preferred method for synthesizing chromene 4 from 5,7-dihydroxy-4-propylcoumarin, 2, is shown in Scheme I. According to this synthetic scheme, 5,7-dihydroxy-4-propylcoumarin, 2,[5] was prepared quantitatively from ethyl butyrylacetate and phloroglucinol under Pechmann conditions.[6]

In conducting this reaction, a volume of a concentrated acid is added in a dropwise manner to a stirring mixture of ethyl butyrylacetate and phloroglucinol with a mole ratio ranging between about 3:1 and about 1:3, with a preferable range being about 0.9:1.0. The dropwise addition of an acid was conducted at a rate such that the temperature of the reaction mixture is maintained at a temperature ranging between about 0° C. and about 120° C., preferably about 90° C.

Suitable, but not limiting, examples of concentrated acid include sulfuric acid, trifluoroacetic acid, and methanesulfonic acid. In practicing this invention, concentrated sulfuric acid is particularly preferred. As the product yield and purity appear to be dependent on the amount of concentrated sulfuric acid used, it is preferred that the amount of concentrated sulfuric acid range between about 0.5 and 10 moles, most preferably ranging between about 2 and about 3.5 moles, per mole of ethyl butyrylacetate.

The reaction mixture is then heated to a temperature ranging between about 40° C. and about 150° C., preferably about 90° C., until the reaction reaches completion as determined by TLC analysis. The reaction mixture is then poured onto ice and the precipitated product is collected by filtration and dissolved in an organic solvent. Suitable, but non-limiting, examples of organic solvents include ethyl acetate, chloroform, and tetrahydrofuran. A preferred solvent is ethyl acetate. The resulting solution is then washed with brine and dried over a suitable drying agent, e.g., sodium sulfate. The yields of this reaction are generally quantitative.

Thereafter, 5,7-dihydroxy-8-propionyl-4-propylcoumarin, 3, was prepared by selectively acylating the 8-position of 5,7-diydorxy-4-propylcoumarin, 2, with propionyl chloride in the presence of a Lewis acid catalyst. In conducting this reaction, a solution of propionyl chloride in a suitable solvent, e.g., carbon disulfide, was added in a dropwise manner to a vigorously stirred solution of 5,7-dihydroxy-4-propylcoumarin, 2, a Lewis acid and an organic solvent cooled in an ice bath. Dropwise addition of propionyl chloride is conducted such that the temperature of the reaction mixture is maintained at a temperature ranging between 0° C. and about 30° C., preferably between about 8° C. and 10° C.

In practicing the invention, the amount of propionyl chloride used generally ranges between about 0.5 moles and about 6 moles, preferably ranging between about 1 mole and about 2 moles, per mole of 5,7-dihydroxy-4-propylcoumarin, 2.

Non-limiting examples of Lewis acid catalysts useful in the acylation reaction include $AlCl_3$, $BF_3$, $SnCl_4$, $ZnCl_2$, $POCl_3$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of organic solvent for use in preparing the 5,7-dihydroxy-4-propylcoumarin, 2, solution include nitrobenzene, nitromethane, chlorobenzene, or toluene and mixtures thereof. A preferred organic solvent for use in this invention is nitrobenzene.

Upon completion of the addition of propionyl chloride, the vigorously stirred reaction mixture is maintained at a temperature ranging between about 0° C. and about 120° C., preferably ranging between about 25° C. and 80° C., until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

On a small scale, the yield of 5,7-dihydroxy-8-propionyl-4-propylcoumarin 3, produced by the above described reaction is generally quantitative. However, on a larger scale, the reaction was very difficult to control and did not exclusively afford the desired product. A route developed for the synthesis of Mammea coumarin was initially attempted for the preparation of compound 3, but it proved too awkward and low-yielding.[7]

Since the desired 8-position acylated product 3 was always accompanied by the formation of undesired 6-position acylated product and 6,8-bis-acylated product, it was necessary to optimize the reaction conditions to minimize the formation of the undesired products and develop a more effective purification process to increase the purity and scale-up the quantities of the desired 5,7-dihydroxy-8-propionyl-4-propylcoumarin 3. An alternative and preferred route for preparing 5,7-dihydroxy-8-propionyl-4-propylcoumarin 3 in large scale quantities is then developed.

Preparation of 8-acylated coumarin 3 on a 5 gram scale as a single product (45% yield) has been achieved by adding a mixture of propionic anhydride, a Lewis acid, e.g., $AlCl_3$, and suitable solvent, e.g., 1,2-dichloroethane, into a vigorously stirring pre-heated mixture of coumarin, a Lewis acid, e.g., $AlCl_3$, and suitable solvent, e.g., 1,2-dichloroethane, at a temperature ranging between about 40 and about 160° C., preferably ranging between about 70 and about 75° C. Dropwise addition of the propionic anhydride solution is conducted at a rate such that the temperature of the reaction mixture is maintained within the desired temperature range.

The amount of propionic anhydride used in the reaction generally ranges between about 0.5 and about 10, preferably ranging between about 1 and about 2 moles, per mole of 5,7-dihydroxy-4-propylcoumarin 2.

Non-limiting examples of Lewis acid catalysts useful in the acylation reaction include $AlCl_3$, $BF_3$, $POCl_3$, $SnCl_4$, $ZnCl_2$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 4 moles, per mole of 5,7-dihydroxy-4-propylcoumarin, 2.

Suitable but nonlimiting examples of solvents for use in the invention include diglyme, nitromethane, 1,1,2,2-tetrachloroethane, and 1,2-dichloroethane (preferred).

Upon completion of the addition of propionyl anhydride, the vigorously stirred reaction mixture is maintained at a temperature ranging between about 40° C. and about 160° C., preferably ranging between about 70° C. and 75° C., until the reaction reaches completion as monitored by conventional means such as TLC analysis. The workup procedure is the same as described above.

The product was purified without the use of column chromatography to afford the desired product 3. This procedure has been scaled-up to 1.7 kg of coumarin (for details see experimental section) and the yield for 8-acylated coumarin 3 was 29% after recrystallization. The yield for 8-acylated coumarin 3 may be further improved by changing the purification processing. For example, the crude product may be recrystallized from solvent(s) other than dioxane, or a simple washing with an appropriate solvent may lead to product pure enough for the next reaction step.

Thereafter, chromene 4 was prepared by introducing the chromene ring into 5,7-dihydroxy-8-propionyl-4-propylcoumarin, 3, using 4,4-dimethoxy-2-methylbutan-2-ol. According to the method of the present invention, a solution of 5,7-dihydroxy-8-propionyl-4-propylcoumarin, 3, and 4,4-dimethoxy-2-methylbutan-2-ol in a suitable organic solvent in the presence of a base was reacted at a temperature ranging between about 40° C. and about 180° C., preferably ranging between about 100° C. and about 120° C., until the reaction reached completion as determined by conventional means such as TLC analysis. Water and methanol formed during the reaction were removed azeotropically via a Dean-Stark trap.

In practicing this invention, the amount of 4,4-dimethoxy-2-methylbutan-2-ol employed in the reaction generally ranges between about 0.5 and about 8 moles, preferably ranging between about 2 and about 4 moles, per mole of 5,7-dihydroxy-8-propionyl-4-propylcoumarin 3.

Suitable, but not limiting examples of organic solvents include pyridine, triethylamine, N,N-dimethylformamide (DMF), toluene, tetrahydrofuran (THF) or 1,2-dichloroethane. Suitable, but non-limiting examples of the bases include pyridine, 4-dimethylaminopyridine, triethylamine, N,N-diethylaniline, 1,5-diazabicyclo-[4,3,0]-non-5-ene (DBN), 1,8-diazabicyclo-[5,4,0]undec-7-ene (DBU), sodium carbonate and sodium bicarbonate. Pyridine was used as both base and solvent in this invention on a small scale; for scale-up, however, pyridine was used as a base and toluene was used as a solvent.

Upon completion of the reaction, the solvent is removed under reduced pressure and the reaction products is dissolved in a suitable solvent, e.g., ethyl acetate. The solution is then washed sequentially with water and brine and dried over a suitable drying agent, e.g., sodium sulfate. Thereafter, the crude chromene 4 product can be purified by conventional means such as silica gel column chromatography using 25% ethyl acetate/hexane as the elution solvent. The yields of chromene 4 generally fall with the range of about 60% and about 85%, usually resulting in about 78% yield.

Thereafter, chromanone 7 may be produced by reacting a solution of chromene 4, acetaldehyde diethylacetal, and an acid catalyst in organic solvent at a temperature ranging between about 60° C. and about 140° C., preferably about 140° C., until the reaction is completed.

The amount of acetaldehyde diethylacetal used in the reaction generally ranges between about 0.5 and about 20 moles, preferably ranging between about 3 and about 5 moles, per mole of chromene 4.

Suitable, but non-limiting, examples of acid catalysts include trifluoroacetic acid, methanesulfonic acid, trifluoromethanesulfonic acid, p-tosylic acid, acetic acid, hydrofluoric acid and their pyridinium salts and mixtures thereof. A preferred acid catalyst for the use in this invention is trifluoroacetic acid. The amount of acid catalyst used generally ranges between about 2 and about 25 moles, preferably ranging between about 17 and about 22 moles, per mole of chromene 4.

Two alternative routes for preparing chromanone 7 from chromene 4 in large scale quantities were developed and which involve either a one-step reaction process (paraldehyde one-step reaction) or a two-step reaction processes (LDA/sulfuric acid process or LDA/Mitsunobu process).

(a) Paraldehyde one-step reaction

Instead of acetaldehyde diethylacetal, paraldehyde was used as the acetaldehyde equivalent. In the presence of one or more acid catalysts such as $CF_3SO_3H$, $CF_3CO_2H$, and pyridinium p-toluenesulfonate (PPTS), chromene 4 was reacted with paraldehyde at elevated temperature in a suitable solvent to afford chromanone 7 as the major product and the corresponding 10,11-cis-dimethyl derivative 7a as a minor product.

According to this reaction, paraldehyde was added to a stirring solution of chromene 4 and an acid catalyst, e.g., PPTS, at room temperature in a suitable solvent.

The resulting mixture was heated at the temperature ranging between about 40 and about 140° C., preferably ranging between about 60 and about 100° C., for a period of time ranging between about 5 and about 36 hours, preferably about 20 hours. Thereafter, $CF_3CO_2H$, an additional equivalent of PPTS and paraldehyde was added and the resulting mixture was maintained at a temperature ranging between about 40 and about 140° C., preferably ranging between about 60 and about 100° C. overnight or until the reaction reached completion as determined by convention means, e.g., TLC.

The amount of paraldehyde employed per mole of chromene 4 generally ranges between about 1 and about 40 moles, preferably ranging between about 20 and about 30 moles.

Non-limiting acid catalysts include trifluoromethane sulfonic acid, trifluoroacetic acid, methanesulfonic acid, p-tosylic acid and their pyridinium salts. In practicing this invention, pyridinium p-toluenesulfonate (PPTS) is the preferred acid catalyst. The amount of acid catalyst used in the reaction ranges between about 0.5 and about 10 moles, preferably between about 1 and about 2 moles.

Representative solvents for use in the reaction include toluene, diglyme and 1,2-dichloroethane. In practicing the invention, 1,2-dichloroethane is the preferred solvent.

Upon completion of the reaction, the reaction was neutralized with saturated bicarbonate solution and extracted with a suitable solvent, e.g., ethyl acetate. The crude product was then purified as described above. The yields of chromanone 7 from this reaction generally range between about 20 and about 60%, usually about 40%.

(b) LDA/sulfuric acid two-step reaction

Under aldol condensation conditions, chromene 4 was reacted with acetaldehyde to form an open-chain aldol product 7b. According to the present invention, a solution of LDA in THF was added dropwise to a solution of chromene 4 in THF at a temperature ranging between about −78° C. and about 0° C., preferably about −30° C. and about −78° C. The amount of LDA added per mole of chromene 4 ranged between about 1 and about 4 moles, preferably ranging between about 2 and about 3 per mole of chromene 4. Dropwise addition LDA is conducted such that the reaction temperature is maintained within the desired range.

Acetaldehyde was then added dropwise to the reaction mixture in amounts ranging between about 1 and about 12 moles, preferably ranging between about 4 and about 6 moles per mole of chromene 4. Dropwise addition of acetaldehyde is conducted such that the reaction temperature is maintained within the aforementioned range. The reaction was monitored by conventional means, e.g., TLC analysis, until it reached completion.

One skilled in the art will appreciate that the aldol reaction of chromene 4 with acetaldehyde to form 7b can be carried out under conditions which employs bases other than LDA. For example, metal hydroxides such as NaOH, KOH and $Ca(OH)_2$, metal alkoxides such as MeONa, EtONa and t-BuOK, and amines such as pyrrolidine, piperidine, diisopropylethylamine, 1,5-diazabicyclo[4,3,0]non-5-ene (DBN), 1,8-diazabicyclo[5,4,0]undec-7-ene (DBU), LDA, $NaNH_2$ and LiHMDS as well as hydrides such as NaH and KH can all be employed for the aldol reactions.[15] Also, aldol reactions can be mediated by metal complexes of Al, B, Mg, Sn, Ti, Zn and Zr compounds such as $TiCl_4$, $(i-PrO)_3TiCl$, $(i-PrO)_4Ti$, $PhBCl_2$, $(n-Bu)_2BCl$, $BF_3$, $(n-Bu)_3SnCl$, $SnCl_4$, $ZnCl_2$, $MgBr_2$, $Et_2AlCl$ with or without chiral auxiliaries such as 1,1'-binaphthol, norephedrinesulfonate, camphanediol, diacetone glucose and dialkyl tartrate.[16-18]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product 7b generally range between about 40% and about 80%, usually about 70%.

It should be noted that there are two asymmetric centers in 7b. Therefore, product 7b is racemic mixture of two sets of enantiomers (four optically active forms) which may be resolved by conventional resolution methods such as chromatography or fractional crystallization of suitable diastereoisomeric derivatives such as salts or esters with optically active acids (e.g., camphor-lo-sulfonic acid, camphoric acid, methoxyacetic acid, or dibenzoyltartaric acid) or enzymatically catalyzed acylation or hydrolysis of the racemic esters. Also, chiral transition metal-mediated aldol reactionl[17,18] of chromene 4 with acetaldehyde may directly produce optically active one of the enantiomers of 7b. The resultant or synthetic enantiomer may then be transformed to enantioselective synthesis of (+)-calanolide A and its congeners.

The crude aldol product 7b was then cyclized under acidic conditions to form a mixture of both chromanone 7 and 10,11-cis-dimethyl derivative 7a in a 1:1 ratio. Suitable, but non-limiting, acids include one or more acids such as sulfuric acid, hydrochloric acid (aqueous or anhydrous), trifluoroacetic acid, methanesulfonic acid, trifluoromethanesulfonic acid, p-tosylic acid, acetic acid or their mixture thereof. A preferred acid for use in the reaction is a 1:1 v/v mixture of acetic acid and 50% $H_2SO_4$.

The reaction mixture was cooled, ice water was added and the resulting mixture extracted with a suitable solvent, e.g., ethyl acetate. The pooled organic layers were washed with water, saturated bicarbonate solution and brine. The crude product was concentrated in vacuo and purified by conventional means, e.g., silica gel column using a 2:3 (v/v) ethyl acetate/hexane solvent mixture. The yields of chromanone 7 from this reaction generally range between about 10% and about 40%, usually about 20% based on chromene 4.

One skilled in the are will also appreciate that 10,11-cis-chromanone 7a can be treated with with a base under thermodynamic (equilibrium) conditions so as to afford the corresponding trans-chromanone 7. The suitable, but non-limiting, bases include metal hydroxides such as NaOH, KOH and Ca(OH)$_2$, metal alkoxides such as MeONa, EtONa and t-BuOK, amines such as triethylamine, diisopropylethylamine, pyridine, 4-dimethylaminopyridine, N,N-diethylaniline, pyrrolidine, piperidine, 1,5-diazabicyclo[4,3,0]non-5-ene (DBN), 1,8-diazabicyclo-[5,4,0]undec-7-ene (DBU), LDA and LiHMDS as well as metal hydrides such as NaH and KH.

(c) LDA/Mitsunobu two-step reaction

In a preferred reaction, aldol product 7b may be converted to chromanone 7 as the predominant product under neutral Mitsunobu reaction conditions. In this reaction, diethyl azodicarboxylate (DEAD) was added dropwise to a solution containing crude aldol product 7b and triphenylphosphine at a temperature ranging between about −10° C. and about 40° C., preferably about ambient temperature. The amount of DEAD used in the reaction generally ranges between about 1 and about 10 moles preferably about 1 and about 4 moles, per mole of aldol 7b. The amount of triphenylphosphine used in the reaction generally ranged between about 1 and about moles, preferably ranging between about 1 and about 4 moles, per mole of aldol 7b.

Instead of DEAD, other reagents reported in the literature can be employed such as diisopropyl azodicarboxylate (DIAD), dibutyl azodicarboxylate (DBAD), dipiperidinoazodicarboxamide, bis (N[4]-methylpiperazin-1-yl) azodicarboxamide, dimorpholinoazodicarboxamide, N,N,N'N'-tetramethylazodicarboxamide (TMAD)[19]. Also, in addition to triphenylphosphine, tri-n-butylphosphine,[19] triethylphosphine, trimethylphosphine and tris (dimethylamino)-phosphine have been used.

Thereafter, the reaction was quenched with saturated ammonium chloride upon completion and extracted with a suitable solvent, e.g., ethyl acetate. The pooled organic layers were washed with brine, concentrated in vacuo and the crude chromanone 7 was purified by conventional means as discussed above. The yields of chromanone 7 from the LDA\Mitsunobu reaction generally range between about 30% and about 60%, usually about 50% based on chromene 4.

Suitable, but non-limiting, examples of azo compounds for the Mitsunobu reaction include diethyl azodicarboxylate (DEAD), diisopropyl azodicarboxylate (DIAD), dibutyl azodicarboxylate (DBAD), dipiperidinoazodicarboxamide, bis (N[4]-methylpiperazin-1-yl) azodicarboxamide, dimorpholinoazodicarboxamide, and N,N,N',N'-tetramethylazodicarboxamide (TMAD).

Suitable, but non-limiting, examples of phosphorous derivatives for the Mitsunobu reaction include triphenylphosphine, tri-n-butylphosphine, triethylphosphine, trimethylphosphine and tris (dimethylamino) phosphine.

Finally, mild borohydride reduction of chromanone 7 in the presence of $CeCl_3(H_2O)_7$ produced (±)-calanolide A with the desired stereochemical arrangement. In conducting the reduction reaction, a solution of chromanone 7 was added dropwise into a solution of reducing agent, e.g., sodium borohydride and a metal additive, e.g., $CeCl_3(H_2O)_7$ in ethanol. The rate of addition is such that the reaction mixture temperature is maintained within a range of between about −40° C. and about 60° C., preferably ranging between about 10° C. and about 30° C. Thereafter, the reaction mixture was stirred at a temperature ranging between about −40° C. and about 60° C.

In general, the amount of metal additive, e.g., $CeCl_3(H_2O)_7$ present in the reaction mixture ranged between about 0.1 and about 2 mole, preferably ranging between about 0.5 and about 1 mole, per mole of sodium borohydride. In addition, the amount of sodium reducing agent, e.g., borohydride employed in the reaction generally ranged between about 0.1 and about 12 moles, preferably ranging between about 2 and about 4 moles, per mole of chromanone 7. Suitable, but non-limiting, examples of reducing agents include $NaBH_4$ $LiAlH_4$, (i-Bu)$_2$AlH, (n-Bu)$_3$SnH, 9-BBN, $Zn(BH_4)_2$, $BH_3$, DIP-chloride, selectrides and enzymes such as baker yeast. Suitable, but non-limiting, examples of metal additives include $CeCl_3$, $ZnCl_2$, $AlCl_3$, $TiCl_4$, $SnCl_3$, and $LnCl_3$ and their mixture with triphenylphosphine oxide. In practicing this invention, sodium borohydride as reducing agent and $CeCl_3(H_2O)_7$ as metal additive are preferred.

Thereafter, the reduction mixture was diluted with water and extracted with a suitable solvent, e.g., ethyl acetate. The extract was dried over a suitable drying agent, e.g., sodium sulfate, and concentrated. The resulting residue was then purified by conventional means such as silica gel chromatography, using ethyl acetate/hexane solvent mixtures.

Thus, (±)-calanolide A, 1, was successfully prepared with the desired stereochemical arrangement by treatment of the key intermediate chromene 4 with acetaldehyde diethyl acetal or paraldehyde in the presence of trifluoroacetic acid and pyridine or a two-step reaction including aldol reaction with acetaldehyde and cyclization either under acidic condition or neutral Mitsunobu condition to produce chromanone 7, followed by Luche reduction via chromanone 7 (see Scheme II).

An alternative route for preparing (±)-calanolide A from chromene 4 was attempted. A Robinson-Kostanecki reaction on 4 was conducted with sodium acetate in refluxing acetic anhydride and produced enone 5 in a 65–70% yield (see Scheme II). Enone 5, however, failed to afford (±)-calanolide A when being reduced with borohydride reagents and some transition metal reducing agents, presumably because attack at the pyrone and ring opening occurred preferentially. Treatment of compound 5 with Baker's yeast also resulted in coumarin ring cleavage while tri-n-butyltin hydride reduce enone 5 into enol 6 in a modest yield.

In another embodiment of the invention, methods for resolving (±)-calanolide A into its optically active forms, (+)-calanolide A and (−)-calanolide A, are provided. In one method, (±)-Calanolide A is resolved by high performance liquid chromatography (HPLC) with organic solvent system as a mobile phase. HPLC is performed on a column packed with chiral packing material. Suitable, but not limiting, examples of chiral packing material include amylose carbamate, D-phenylglycine, L-phenylglycine, D-leucine, L-leucine, D-naphthylalanine, L-naphthylalanine, or L-naphthylleucine. These materials may be bounded, either ionically or covalently, to silica sphere which particle sizes ranging between about 5 µm and about 20 µm.

Suitable, but non-limiting, mobile phase includes hexane, heptane, cyclohexane, ethyl acetate, methanol, ethanol, or isopropanol and mixtures thereof. The mobile phase may be employed in isocratic, step gradient or continuous gradient systems at flow rates generally ranging between about 0.5 mL/min. and about 50 mL/min.

Another method for resolving (±)-calanolide A into its optically active forms involves enzyme-catalyzed acylation or hydrolysis. In practicing this invention, enzyme-catalyzed acylation of (±)-calanolide A is preferred. The enzymatic resolution method employs enzymes such as lipase CC (*Candida cylindracea*), lipase AK (*Candida cylindracea*), lipase AY (*Candida cylindracea*), lipase PS (Pseudomonas Species), lipase AP (*Aspergillus niger*), lipase N (*Rhizopus nieveuis*), lipase FAP (*Rhizopus nieveus*), lipase PP (Porcine Pancrease), pig (porcine) liver esterase (PLE), pig liver acetone powder (PLAP), or subtilisin. The preferred enzyme for use in the enzyme-catalyzed acylation reaction is lipase PS-13 (Sigma Corporation, St. Louis, Mo., USA). Immobilized forms of the enzyme on cellite, molecular sieves, or ion exchange resin are also contemplated for use in this method. The amount of enzyme used in the reaction depends on the rate of chemical conversion desired and the activity of the enzyme.

The enzymatic acylation reaction is carried out in the presence of an acylating agent. Suitable, but not limiting, examples of acylating agents include vinyl acetate, vinyl propionate, vinyl butyrate, acetic anhydride, propionic anhydride, phthalic anhydride, acetic acid, propionic acid, hexanoic acid or octanoic acid. The enzyme reaction employs at least one mole of acylating agent per mole of (±)-calanolide A. Acylating agent can be used as a solvent in the acylation reaction or as a co-solvent with another solvent such as hexanes, chloroform, benzene and THF.

One skilled in the art will appreciate that racemic esters of calanolide A can be made by conventional esterification means and selectively hydrolyzed by the enzymes so as to produce, in high enantiomeric excess, optically active (+)- or (−)-calanolide A in free or esterified form. The esterified calanolide A may be hydrolyzed chemically or enzymatically into the free form. Suitable, but not limiting examples of solvents for use in the enzymatic hydrolysis reaction include water, suitable aqueous buffers such as sodium phosphate buffers or alcohols such as methanol or ethanol.

In yet another embodiment of the invention, a method for treating or preventing viral infections using (±)- and (−)-calanolide A is provided. (±)-Calanolide A and (−)-calanolide A have not been reported before for their anti-HIV activity. It has been discovered that (±)-calanolide A inhibits human immunodeficiency virus type 1 (HIV-1) with $EC_{50}$ value being approximately half of that for (+)-calanolide A. (−)-Calanolide A does not exhibit a synergistic effect on toxicity of (+)-calanolide A. Therefore, one skilled in the art will appreciate to directly use the synthetic (±)-calanolide A as antiviral agent, without further resolution into the optically pure (+)-calanolide A, to inhibit the growth or replication of viruses in a mammal. Examples of mammals include humans, primates, bovines, ovines, porcines, felines, canines, etc. Examples of viruses may include, but not limited to, HIV-1, HIV-2, herpes simplex virus (type 1 and 2) (HSV-1 and 2), varicella zoster virus (VZV), cytomegalovirus (CMV), papilloma virus, HTLV-1, HTLV-2, feline leukemia virus (FLV), avian sarcoma viruses such as rous sarcoma virus (RSV), hepatitis types A-E, equine infections, influenza virus, arboviruses, measles, mumps and rubella viruses. More preferably the compounds of the present invention will be used to treat a human infected with a retrovirus. Preferably the compounds of the present invention will be used to treat a human exposed or infected (i.e., in need of such treatment) with the human immunodeficiency virus, either prophylactically or therapeutically.

An advantage of certain compounds of the present invention is that they retain the ability to inhibit certain HIV RT mutants which are resistant to other non-nucleoside inhibitors such as TIBO and nevirapine or resistant to nucleoside inhibitors. This is advantageous over the current AIDS drug therapy, where biological resistance often develops to nucleoside analogs used in the inhibition of RT.

Hence the compounds of the present invention are particularly useful in the prevention or treatment of infection by the human immunodeficiency virus and also in the treatment of consequent pathological conditions associated with AIDS. Treating AIDS is defined as including, but not limited to, treating a wide range of states of HIV infection: AIDS, ARC, both symptomatic and asymptomatic, and actual or potential exposure to HIV. For example, the compounds of this invention are useful in treating infection of HIV after suspected exposure to HIV by e.g., blood transfusion, exposure to patient blood during surgery or an accidential needle stick.

Antiviral (±)-calanolide A and (−)-calanolide A may be formulated as a solution of lyophilized powders for parenteral administration. Powders may be reconstituted by addition of a suitable diluent or other pharmaceutically acceptable carrier prior to use. The liquid formulation is generally a buffered, isotonic, aqeuous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium chloride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, or collodial silicon dioxide. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of antiviral (±)-calanolide A and (−)-calanolide A are those to produce the desired affect whereby symptoms of infection are ameliorated. For example, as used herein, a pharmaceutically effective amount for HIV infection refers to the amount administered so as to maintain an amount which suppresses or inhibits secondary infection by syncytia formation or by circulating virus throughout the period during which HIV infection is evidenced such as by presence of anti-HIV antibodies, presence of culturable virus and presence of p24 antigen in patient sera. The presence of anti-HIV antibodies can be determined through use of standard ELISA or Western blot assays for, e.g., anti-gp120, anti-gp41, anti-tat, anti-p55, anti-p17, antibodies, etc. The dosage will generally vary with age, extent of the infection, the body weight and counterindications, if any, for example, immune tolerance. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 50 mg/kg/day, but preferably between about 0.01 to about 1.0 mg/kg/day.

The pharmaceutical composition may contain other pharmceuticals in conjunction with antiviral (±)-calanolide A and (−)-calanolide A, to treat (therapeutically or prophylactically) AIDS. For example, other pharmaceuticals may include, but are not limited to, other antiviral compounds (e.g., AZT, ddC, ddI, D4T, 3TC, acyclovir, gancyclovir, fluorinated nucleosides and nonnucleoside analog compounds[2g] such as TIBO derivatives, nevirapine, pyrridinones, BHAP, HEPTs, TSAOs, α-APA; α-interferon and recombinant CD4), immunostimulants (e.g., various interleukins and cytokines), immunomodulators and antibiotics (e.g., antibacterial, antifungal, anti-pneumocysitis agents). Administration of the inhibitory compounds with other anti-retroviral agents that act against other HIV proteins such as protease, intergrase and TAT will generally inhibit most or all replicative stages of the viral life cycle.

In addition, the compounds of the present invention are useful as tools and/or reagents to study inhibition of retroviral reverse transcriptases. For example, the instant compounds selectively inhibit HIV reverse transcriptase. Hence, the instant compounds are useful as a structure-activity relationship (SAR) tool to study, select and/or design other molecules to inhibit HIV.

The following examples are illustrative and do not serve to limit the scope of the invention as claimed.

EXPRIMENTAL

All chemical reagents and solvents referred to herein are readily available from a number of commercial sources including Aldrich Chemical Co. or Fischer Scientific. NMR spectra were run on a Hitachi 60 MHz R-1200 NMR spectrometer or a Varian VX-300 NMR spectrometer. IR spectra were obtained using a Midac M series FT-IR instrument. Mass spectral data obtained using a Finnegan MAT 90 mass spectrometer. All melting points are corrected.

EXAMPLE 1

5,7-Dihydroxy-4-propylcoumarin[5] (2)

Concentrated sulfuric acid (200 mL) was added into a mixture of phloroglucinol dihydrate (150 g, 0.926 mol) and ethyl butyrylacetate (161 g, 1.02 mol). The resulting mixture was stirred at 90C for two hours whereupon it was poured onto ice. The solid product was collected by filtration, and then dissolved in ethyl acetate. The solution was washed with brine and dried over $Na_2SO_4$. After removal of the solvent in vacuo, the residue was triturated with hexane to provide essentially pure compound 2 (203 g) in quantitative yield, mp 233–235° C. (Lit.[5] 236–238° C.). $^1$H-NMR[5] (DMSO-$d_6$) δ 0.95 (3H,t,J=6.9 Hz, $CH_3$); 1.63 (2H, apparent hextet, J=7.0 Hz, $CH_2$); 2.89 (2H,t,J=7.5 Hz,$CH_2$); 5.85 (1H, s, $H_3$); 6.22 (1H, d, J=2.0 Hz, $H_6$); 6.31 (1H, d, J=2.0 Hz, $H_8$); 10.27 (1H, s, OH); 10.58 (1H, s, OH); MS (EI); 220(100, M+); 205 (37.9, M—$CH_3$); 192 (65.8, M—$C_2H_4$); 177 (24.8, M—$C_3H_7$); 164 (60.9, M—$CHCO_2$+1); 163 (59.6 M—$CHCO_2$); IR (KBr): 3210 (vs and broad, OH); 1649 (vs, sh); 1617 (vs, sh); 1554 (s) $cm^{-1}$); Anal. calcd. for $C_{12}H_{24}O_4$: C, 65.45; H, 5.49; Found: C, 65.61; H, 5.44.

EXAMPLE 2

5,7-Dihydroxy-8-propionyl-4-propylcoumarin (3)

A three-neck flask (500 mL) equipped with an efficient methanical stirrer, thermometer and addition funnel was charged with 5,7-dihydroxy-4-propylcourmarin, 2, (25.0 g, 0.113 mol), aluminum chloride (62.1 g; 0.466 mol), and nitrobenzene (150 mL) and the mixture was stirred until a solution was obtained, which was cooled to 0° C. in an ice bath. A solution of propionyl chloride (15.2 g; 0.165 mol) in carbon disulfide (50 mL) was added dropwise at such a rate that the reaction temperature was maintained at 8–10° C. Addition was completed over a period of 1 hour with vigorous stirring. The reaction was monitored by TLC using a mobile phase of 50% ethyl acetate/hexane. After three hours, an additional portion of propionyl chloride (2.10 g; 0.0227 mol) in carbon disulfide (10 mL) was added. Immediately after the TLC analysis indicated the total consumption of starting material, the reaction mixture was poured onto ice, and allowed to stand overnight. The nitrobenzene was removed by steam distillation, and the remaining solution was extracted several times with ethyl acetate. The extracts were combined and dried over $Na_2SO_4$. The crude product obtained by evaporation in vacuo was purified by chromatography on a silica gel column eluting with 50% ether/hexane to provide the desired propionylated coumarin 3, mp (corr) 244–246° C. $^1$H-NMR (DMSO-$d_6$) δ 0.96 (3H, t, J=7.3 Hz, $CH_3$); 1.10 (3H, t, J=7.2 Hz, $CH_3$); 1.60 (2H, m, $CH_2$); 2.88 (2H, t, J=7.7 Hz, $CH_2$); 3.04 (2H, q, J=7.2 Hz, $CH_2$); 5.95 (1H, s, $H_3$); 6.31 (1H, s, $H_6$); 11.07 (1H, s, OH); 11.50 (1H, s, OH); MS (EI): 277 (6.6, M+1); 276 (9.0, M+); 247 (100, M—$C_2H_5$); IR (KBr): 3239 (s and broad, OH); 1693 (s, C=O), 1625 and 1593 (s) $cm^{-1}$; Anal. calcd. for $C_{15}H_6O_5$: C, 65.21; H, 5.84; Found: c, 64.92; H, 5.83. The isomer assignment was made by analogy to precedent.[7]

EXAMPLE 3

2,2-Dimethyl-5-hydroxy-6-propionyl-10-propyl-2H, 8H-benzo[1,2-b:3,4-b']dipyran-8-one (4)

A mixture of 3 (2.60 g, 9.42 mmol) and 4,4-dimethoxy-2-methylbutan-2-ol (5.54 g, 37.7 mmol) were dissolved in anhydrous pyridine (6.5 mL). The mixture was refluxed under nitrogen for three days. After removal of the solvent in vacuo, the residue was dissolved in ethyl acetate. The ethyl acetate was washed several times with 1 N HCl and brine. It was then dried over $Na_2SO_4$. The crude product obtained by evaporation in vacuo was purified by silica gel column chromatography, eluting with 25% ethyl acetate/hexane to afford 2.55 g of 4 in 78.6% yield, mp 96–98° C. $^1$H-NMR (CDCl$_3$) δ 1.05 (3H, t, J=7.3 Hz, CH$_3$); 1.22 (3H, t, J=7.5 Hz, CH$_3$); 1.53 (6H, s, 2 CH$_3$); 1.75 (2H, m, CH$_2$); 2.92 (2H, t, J=7.1 Hz, CH$_2$); 3.35 (2H, q, J=7.1 Hz, CH$_2$); 5.56 (1H, d, J=10.0 Hz, H$_3$); 5.98 (1H, s, H$_9$); 6.72 (1H, d, J=10.0 Hz, H$_4$); MS (EI): 343 (5.7, M+1); 342 (22.5, M+); 327 (100, M—CH$_3$); IR (KBr): 1728 (vs, C=O) cm–1; Anal. calcd. for $C_{20}H_{22}O_5$: C, 70.16; H, 6.48; Found: C, 70.45; H, 6.92.

EXAMPLE 4

10,11-Didehydro-12-oxocalanolide A (5)

A mixture of 4 (1.76 g, 5.11 mmol) and sodium acetate (0.419 g, 5.11 mmol) in acetic anhydride (12 mL) were refluxed for 10 hours whereupon the solvent was removed in vacuo. The residue was purified by silica gel column chromatography, eluting first with 25% ethyl acetate/hexane followed by 50% ethyl acetate/hexane to provide 1.16 g (62% yield) of enone 5 (6,6,10,11-tetramethyl-4-propyl-2H,6H,12H-benzo[1,2-b:3,4-b':5,6-b"]-tripyran-2,12-dione) as a white solid, mp 209–209.5° C. $^1$H-NMR (CDCl$_3$) δ 1.05 (3H, t, J=6.6 Hz, CH$_3$); 1.56 (6H, s, 2 CH$_3$); 1.73 (2H, m, CH$_2$); 1.98 (3H, s, CH$_3$); 2.38 (3H, s, CH$_3$); 2.91 (2H, t, J=7.5 Hz, CH$_2$); 5.69 (1H, d, J=10.0 Hz, H$_7$); 6.11 (1H, s, H$_3$); 6.71 (1H, d, J=10 Hz, H$_8$); MS (EI): 366 (29.6, M+); 351 (100, M—CH$_3$); 323 (16.5, M—C$_3$H$_7$); IR (KBr): 1734 (vs, C=O), 1657, 1640, 1610, and 1562 cm$^{-1}$; Anal. calcd. for $C_{22}H_{22}O_5$: 72.12; H, 6.05; Found: C, 72.14; H, 6.15.

EXAMPLE 5

10,11-Didehydrocalanolide A (6)

A mixture of enone 5 (160 mg, 0.437 mmol) and tri-n-butyltin hydride (0.318 g, 1.09 mmol) in dry dioxane (2.0 mL) was refluxed under nitrogen for 12 hours. The solvent was then removed in vacuo and the residue was purified by preparative TLC using 25% ethyl acetate in hexane as the mobile phase. The product exhibited an R$_f$ of about 0.4. Enol 6 (12-hydroxy-6,6,10,11-tetramethyl-4-propyl-2H,6H,12H-benzo[1,2-b:3,4-b':5,6-b"]-tripyran-2-one) (13.3 mg, 8%) was isolated as an oil from the plate by ethyl acetate elution. This elution may have been inefficient, and the actual yield higher, as indicated by analytical TLC of the crude product. $^1$H-NMR (CDCl$_3$) δ 0.92 (3H, t, J=6.0 Hz, CH$_3$); 1.26 (3H, s, CH$_3$); 1.39 (3H, s, CH$_3$); 1.63 (2H, m, CH$_2$); 1.96 (3H, s, CH$_3$); 2.36 (3H, s, CH$_3$); 2.45 (2H, t, J=6.0 Hz, CH$_2$); 3.65 (1H, s, H$_{12}$); 5.51 (1H, d, J=10.0 Hz, H$_7$); 6.67 (1H, d, J=10.0 Hz, H$_8$); 13.25 (1H, br s, OH); MS (EI): 369 (3.8, M+1), 368 (4.4, M+), 367 (8.3, M–1) 366 (28.4, M–2), 351 (100, M—OH); IR(KBr): 1651 20 (s), 1589 (m)cm$^{-1}$.

EXAMPLE 6

12-Oxocalanolide A (7)

A solution containing chromene 4 (344 mg, 1.0 mmol), acetaldehyde diethylacetal (473 mg, 4.0 mmol), trifluoroacetic acid (1.5 mL, 19.4 mmol) and anhydrous pryidine (0.7 mL) was heated at 140° C. under N$_2$. The reaction was monitored by TLC analysis. After 4 hours, the reaction mixture was cooled to room temperature, diluted with ehtyl acetate and washed several times with 10% aqueous NaHCO$_3$ and brine. The organic layer was separated and dried over Na$_2$SO$_4$. The solvent was removed in vacuo and the crude product was purified by silica gel column chromatography eluting with ethyl acetate/hexane (2:3). Chromanone 7 (10,11-trans-dihydro-6,6,10,11-tetramethyl-4-propyl-2H,6H,12H-benzo[1,2-b:3,4-b':5,6-b"]-tripyran-2,12-dione) (110 mg, 30% yield) was obtained m.p. 176~177° C. (Lit.[5] 130~132° C.). $^1$H-NMR[5] (CDCl$_3$) δ 1.02 (3H, t, J=7.5 Hz, CH$_3$); 1.21 (3H, d, J=6.8 Hz, CH$_3$); 1.51 (3H, d, J=7.0 Hz, CH$_3$); 1.55 (6H, 2s, 2 CH$_3$); 1.63 (2H, sextet, J=7.0 Hz, CH$_2$); 2.55 (1H, dq, J=6.9 Hz, J=11.0 Hz, H$_{11}$); 2.88 (2H, t, J=7.6 Hz, CH$_2$); 4.28 (1H, dq, J=6.3 Hz, J=11.0 Hz, H$_{10}$); 5.60 (1H, d, J=9.9 Hz, H$_8$); 6.04 (1H, s, H$_3$); 6.65 (1H, d, J=11.8 Hz, H$_7$); MS (CI): 369 (100, M+1).

EXAMPLE 7

(±)-Calanolide A (1)

To a solution of chromanone 7 (11 mg, 0.03 mmol) in EtOH (0.4 mL) was added sodium borohydride (2.26 g, 0.06 mmol) and CeCl$_3$(H$_2$O)$_7$ (11.2 mg, 0.03 mmol) in EtOH (5 mL) at room temperature. After stirring for 45 minutes, the mixture was diluted with H$_2$O and extracted with ethyl acetate. The organic layer was dried over Na$_2$SO$_4$ and concentrated. The crude product was purified by preparative TLC eluting with ethyl acetate/hexane (1:1) to afford (±)-calanolide A (1) (10.5 mg, 94%). m.p. 52≧54° C., which increased to 102° C. after it was dried thoroughly (Lit.[5] 56–58° C.). $^1$H NMR (CDCl$_3$): δ 1.03 (3H, t, J=7.3 Hz, CH$_3$) 1.15 (3H, d, J=6.8 Hz, CH$_3$), 1.46 (3H, d, j=6.8 Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.52 (1H, broad-s, OH), 3.93 (1H, m, H$_{10}$), 4.72 (1H, d, J=7.8 Hz, H$_{12}$), 5.54 (1H, d, J=10.0 Hz, H$_7$), 5.94 (1H, s, H$_3$), 6.62 (1H, d, J=9.9 Hz, H$_8$); MS (CI): 371 (75.4, M+1), 370 (16.1, M$^+$), 353 (100, M—OH); Anal. calcd. for $C_{22}H_{25}O_5$: C, 71.33; H, 7.07: Found: C, 71.63; H, 7.21.

EXAMPLE 8

5,7-Dihydroxy-4-propylcoumarin (2)

In this Example, kilogram scale preparation of intermediate 2 is described. Into a stirring suspension of phloroglucinol (3574.8 g, 28.4 mol, pre-dried to constant weight) and ethyl butyrylacetate (4600 mL, 28.4 mol) was added concentrated sulfuric acid dropwise at such a rate that the internal temperature did not exceed 40° C. After 100 mL of sulfuric acid was added, the temperature rose to 70° C. and the suspension turned into a yellow solid. Analysis of TLC indicated that the reaction had proceeded to completion. The reaction mixture was diluted with water (10 L) and stirred at ambient temperature overnight. The precipitated product was collected by filtration and then rinsed with water until the filtrate was neutral. A quantity of 4820 g (77% yield) of 5,7-dihydroxy-4-propylcoumarin 2 was obtained after being dried, which was identical with an authentic sample by comparison of TLC, melting point and spectroscopic data.

EXAMPLE 9

5,7-Dihydroxy-8-propionyl-4-propylcoumarin 3

In this Example, kilogram quantities of intermediate 3 was sythesized using propionic anhydride instead of propionyl chloride. 5,7-dihydroxy-4-propyl-coumarin, 2, (1710 g, 7.77 mol) and $AlCl_3$ (1000 g, 7.77 mol) were mixed in 1,2-dichloroethane (9 L). The resulting orange suspension was stirred and heated to 70° C. until a solution was obtained. Then, a mixture of propionic anhydride (1010 g. 7.77 mol) and $AlCl_3$ (2000 g, 15.54 mol) in 1,2-dichloroethane (3.4 L) was added dropwise over 3 h. The reaction was allowed to stir at 70° C. for an additonal hour. After being cooled down to room temperature, the reaction mixture was poured into a rapidly stirring mixture of ice water and 1N HCl. The precipitated product was taken into ethyl acetate (30 L) and the aqueous solution was extracted with the same solvent (10 L×2). The combined extracts were successively washed with 1 N HCl (10 L), saturated aq. $NaHCO_3$ (10 L), and water (10 L). After being dried over $MgSO_4$ and concentrated in vacuo, a solid product (1765 g) was obtained which was washed with ethyl acetate (15 L) and recrystallized from dioxane (9.5 L) to provide 514 g of pure compound 3. From the ethyl acetate washings, an additional 100 g of compound was obtained after recrystallization from dioxane. Thus, the combined yield for compound 3, which was identical with an authentic sample by comparison of TLC, melting point and spectroscopic data, was 29%.

EXAMPLE 10

2,2-Dimethyl-5-hydroxy-6-propionyl-10-propyl-2H, 8H-benzo[1,2-b:3,4-b']dipyran-8-one (4):

In this Example, intermediate 4 was prepared in half kilogram quantities from 3 via modification of the reaction conditions described in Example 3. A mixture of compound 3 (510.6 g, 1.85 mol) and 4,4-dimethoxy-2-methylbutan-2-ol (305.6 g, 2.06 mol) were dissolved in a mixture of toluene (1.5 L) and dry pyridine (51 mL). This mixture was stirred and refluxed; water and MeOH formed during the reaction were removed azeotropically via a Dean-Stark trap. The reaction was monitored by TLC. After 6 days, the reaction had proceeded to completion. The mixture was then cooled to ambient temperature and diluted with ethyl acetate (L) and 1 N HCl (1 L). The ethyl acetate solution was separated and washed with 1N HCl (500 mL) and brine (1L). After being dried over $Na_2SO_4$ and evaporated in vacuo, a quantity of 590 g (93% yield) of compound 4 was obtained which was greater than 95% pure without further purification and was compared with an authentic sample by TLC and spectroscopic data. No trace of 6-acylated or 6,8-bisacylated product was observed, although a small amount of 7-monoester did form.

EXAMPLE 11

12-Oxocalanolide A (7)

In this Example, chromanone 7 was prepared from two alternative pathways involving either a one-step reaction (procedure A) or a two-step reaction process (procedures B and C).
Procedure A.
Paraldehyde One-Step Reaction:
To a stirring solution of chromene 4 (350 mg, 1.0 mmol) and PPTS (250 mg, 1.0 mmol) in 1,2-dichloroethane (2 mL) at ambient temperature under $N_2$ was added 3 mL paraldehyde (22.5 mmol). The resulting mixture was refluxed for 7 h. Then, $CF_3CO_2H$ (1 mL), an additional equivalent of PPTS and 1 mL of paraldehyde were added; the mixture was refluxed overnight. The reaction mixture was neutralized with saturated aqueous $NaHCO_3$ and extracted with ethyl acetate (50 mL×3). The crude product obtained by evaporation under reduced pressure was washed with hexane. The residue was purified by column chromatography eluting with ethyl acetate/hexane (1:2) to afford 100 mg (27% yield) of chromanone 7 and 30 mg (8% yield) of 7a. Chromanone 7 (10,11-trans-dihydro-6,6,10,11-tetramethyl-4-propyl-2H, 6H,12H-benzo[1,2-b:3,4-b':5,6-b"] tripyran-2,12-dione) obtained by this method was identical with an authentic sample by comparison of TLC, HPLC and spectroscopic data.
Procedure B
LDA/Sulfuric Acid Two-Step Reaction:
To a stirring solution of chromene 4 (5.0 g, 14.6 mmol) in THF (75 mL) at −30° C. under $N_2$ was added 18.3 mL (36.5 mmol) of 2 M LDA in THF. After 15 min at the same temperature, acetaldehyde (5.0 mL, 89.5 mmol) was added via syringe. The reaction was monitored by TLC analysis. After 1 h, the reaction mixture was quenched at −10° C. with saturated aqueous $NH_4Cl$ (75 mL) and extracted with ethyl acetate (125 mL×3). The combined extracts were washed with brine (125 mL) and dried over $Na_2SO_4$. Removal of solvents in vacuo afforded a reddish oil of 7b (8.5 g).

The crude 7b was dissolved in acetic acid (100 mL) and then 50% $H_2SO_4$ (100 mL) was added with stirring. The resulting mixture was heated at 75° C. for 2.5 h and then at 50° C. for 4 h. TLC analysis indicated that the starting material had been consumed. The reaction mixture was determined to contain both chromanone 7 and 10,11-cis-dimethyl derivative 7a in a 1:1 ratio. After cooling to ambient temperature, the reaction mixture was poured into a mixture of ice water (500 mL) and ethyl acetate (500 mL). The layers were separated and the aqueous layer was extracted with ethyl acetate (200 mL×3). The ethyl acetate solutions were combined and washed with saturated aqueous $NaHCO_3$ and brine. After being concentrated in vacuo, the product was purified by chromatography on a silica gel column eluting with ethyl acetate/hexane (2:3) to provide 850 mg (16% yield) of chromanone 7, which was further purified by recrystallization from ethyl acetate/hecane and was identical with an authentic sample by comparison of TLC, HPLC and spectroscopic data.
Procedure C.
LDA/Mitsunobu Two-SteD Reaction:
Into a stirring solution of THF (10 mL) containing triphenylphosphine (1.27 g, 4.80 mmol) and the crude 7b, obtained from chromene 4 (1.0 g, 2.34 mmol), 2.5 equivalents of LDA and 6.0 equivalents of acetaldehyde by the procedure described above, was added dropwise diethyl azodicarboxylate (DEAD, 0.77 mL, 4,89 mmol). The resulting reddish solution was stirred at ambient temperature under $N_2$ for 1 h, after which the reaction mixture was quenched with saturated aqueous $NH_4Cl$ and extracted with ethyl acetate (50 mL×3). The extracts were washed with brine and dried over $Na_2SO_4$. After removal of solvents, the crude product was purified by column chromatography on silica gel eluting with ethyl acetate/hexane (2:3) to provide 412 mg (48% yield, based on chromene 4) of chromanone 7, the predominant product of the reaction, which was identical with an authentic sample by comparison of TLC, HPLC and spectroscopic data.

EXAMPLE 12

(±)-Calanolide A (1)

In this Example, (±)-calanolide A was prepared in multigram scale using the procedure described in Example 7. To a stirring solution of chromanone 7 (51.5 g, 0.14 mol) in EtOH (1.5 L) was added $CeCl_3(H_2O)_7$ (102 g, 274 mmol). The mixture was stirred for 1.5 h at room temperature under $N_2$ and then cooled to −30° C. with an ethylene glycol/$H_2O$ (1:2 w/w) dry ice bath. After the temperature was equilibrated to −30° C., $NaBH_4$ (21.3 g, 563 mmol) was added and stirred at the same temperature for 8.5 h, at which time the reaction was quenched with $H_2O$ (2 L) and extracted with ethyl acetate (2 L×3). The extracts were combined, washed with brine (2 L) and dried over $Na_2SO_4$. The crude product obtained by removal of solvent under reduced pressure was passed through a short silica gel column to provide 53 g of mixture which contained 68% of (±)-calanolide A, 14% of calanolide B and 13% of chromanone 7 as shown by HPLC. This material was subjected to further purification by preparative HPLC to afford pure (±)-calanolide A (1).

EXAMPLE 13

Chromatographic Resolution of Synthetic (±)-Calanolide A

Figure 6A:
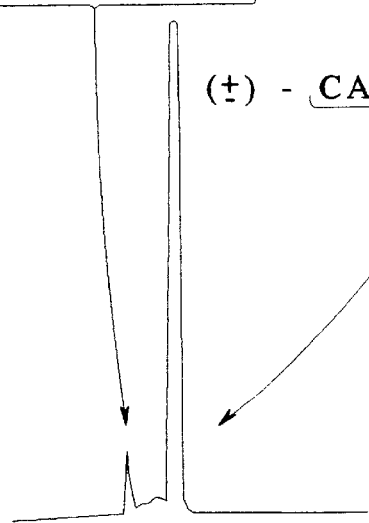
FIG. 6 is an HPLC chromatogram of 6(a) (±)-calanolide A on normal phase column; 6(b) (±)-calanolide A on a chiral HPLC column; 6(c) (+)-calanolide A on a chiral HPLC column and 6(d) (−)-calanolide A on on a chiral HPLC column. The HPLC conditions are described in Example 13.
Figure 6B:
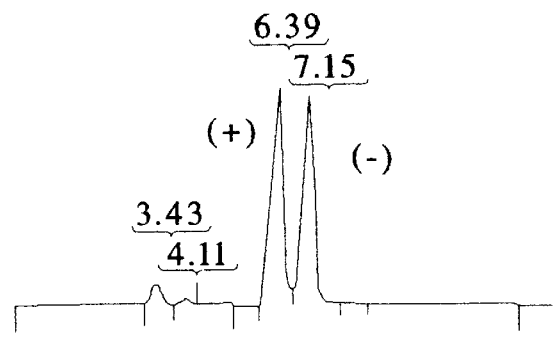
Figure 6C:
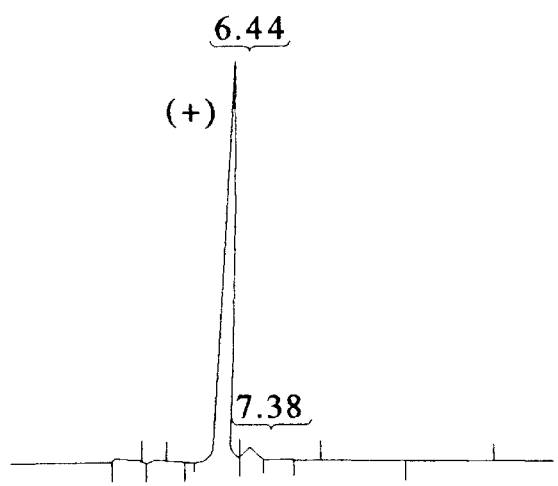
Figure 6D:
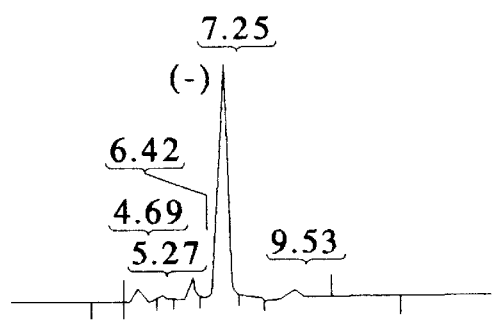

The synthetic (±)-1 was resolved into enantiomers, (+)-calanolide A and (−) calanolide A, by preparative HPLC. Thus, using a normal phase silica gel HPLC column (250 mm×4.6 mm I. D. Zorbasil, 5 μm particle size, MAC-MOD Analytical, Inc., PA, USA), the synthetic (±)-1 appeared as one peak with a retention time of 10.15 minutes when hexane/ethyl acetate (70:30) was used as the mobile phase at a flow rate of 1.5 mL/min and a wavelength of 290 nm was used as the uv detector setting. However, on a chiral HPLC column packed with amylose carbamate (250 mm×4.6 mm I. D. Chiralpak A D, 10 μm particle size, Chiral Technologies, Inc., PA, USA), two peaks with retention times of 6.39 and 7.15 minutes in a ratio of 1:1 were observed at a flow rate of 1.5 mL/min. The mobile phase was hexane/ethanol (95:5) and the uv detector was set at a wavelength of 254 nm. These two components were separated using a semi-preparative chiral HPLC column, providing the pure enantiomers of calanolide A. The chemical structures of the separated enantiomers, which were assigned based on their optical rotations and compared with the reported natural product, were characterized by spectroscopic data. HPLC chromatograms (±)-calanolide A and its optical forms are shown in FIG. 6.

(±)-Calanolide A (1): mp 47–50° C. (Lit.[14] 45–48° C.);$[\alpha]^{25}_D$=+68.8° ($CHCl_3$, c 0.7) (Lit.[14] $[\alpha]^{25}_D$=+66.60° ($CHCl_3$, c 0.5); $^1$H NMR ($CDCl_3$) δ 1.03 (3H, t, J=7.3 Hz, $CH_3$), 1.15 (3H, d, J=6.8 Hz, $CH_3$), 1.46 (3H, d, J=6.4 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.52 (1H, d, J=2.9 Hz, OH), 3.93 (1H, m, $H_{10}$), 4.72 (1H, dd, J=7.8 Hz, J=2.7 Hz, $H_{12}$), 5.54 (1H, d, J=9.9 Hz, $H_7$), 5.94 (1H, s, $H_3$), 6.62 (1H, d, J=9.9 Hz, Hg); $^{13}$C NMR ($CDCl_3$) δ 13.99 ($CH_3$), 15.10 ($CH_3$), 18.93 ($CH_3$), 23.26 ($CH_2$), 27.38 ($CH_3$), 28.02 ($CH_3$), 38.66 ($CH_2$), 40.42 (CH), 67.19 (CH—OH), 77.15 (CH—O), 77.67 (C—O), 104.04 ($C_{4a}$), 106.36 ($C_{8a}$ and $C_{12a}$), 110.14 ($C_3$), 116.51 ($C_8$), 126.97 ($C_7$), 151.14 ($C_{4b}$), 153.10 ($C_{8b}$), 154.50 ($C_{12b}$), 158.88 ($C_4$), 160.42 (C=O); CIMS: 371 (100, M+1), 370 (23.6,M$^+$), 353 (66.2, M—OH); 1R: 3611 (w) and 3426 (m, broad, OH), 1734 (vs. C=O), 1643 (m), 1606 (m) and 1587 (vs) cm$^{-1}$; UV $\lambda_{max}$ (MeOH): 204 (32,100), 228 (23,200), 283 (22,200), 325 (12,700) nm; Anal. calcd. for $C_{22}H_{26}O_5 \cdot 1/4H_2O$: C, 70.47; H, 7.12; Found: C, 70.64; H, 7.12.

(−)-Calanolide A (1): mp 47–50° C.;$[\alpha]^{25D}$=−75.6° ($CHCl_3$, c 0.7) Lit.[14] $[\alpha]^{25D}$=−66° ($CHCl_3$, c 0.5); $^1$H NMR ($CDCl_3$) δ 1.03 (3H, t, J=7.4 Hz, $CH_3$), 1.15 (3H, d, J=6.8 Hz, $CH_3$), 1.46 (3H, d, J=6.3 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.50 (1H, d, J=2.9 Hz, OH), 3.92 (1H, m, $H_{10}$), 4.72 (1H, dd, J=7.8 Hz, J=2.7 Hz, $H_{12}$), 5.54 (1H, d, J=10.0 Hz, H7), 5.94 (1H, s, $H_3$), 6.62 (1H, d, J=10.0 Hz, $H_8$); $^{13}$C NMR ($CDCl_3$) δ 13.99 ($CH_3$), 15.10 ($CH_3$), 18.93 ($CH_3$), 23.36 ($CH_2$), 27.38 ($CH_3$), 28.02 ($CH_3$), 38.66 ($CH_2$), 40.42 (CH), 67.19 (CH—OH), 77.15 (CH—)), 77.67 (C-0), 104.04 ($C_{4a}$), 106.36 ($C_{8a}$ and $C_{12a}$), 110.14 ($C_3$), 116.51 ($C_8$), 126.97 ($C_7$), 151.14 ($C_{4b}$), 153.11 ($C_{8b}$), 154.50 ($C_{12b}$), 158.90 ($C_4$), 160.44 (C=O); CIMS: 371 (95.2, M+1), 370 (41.8,M$^+$), 353 (100, M—OH); IR: 3443 (m, broad, OH), 1732 (vs, C=O), 1643 (m), 1606 (m) and 1584 (vs) cm$^{-1}$; UV $\lambda_{max}$ (MeOH): 200 (20,500), 230 (19,400), 283 (22,500), 326 (12,500) nm; Anal. calcd. for $C_{22}H_{26}O_5 \cdot 1/4H_2O$: C, 70.47; H, 7.12; Found: C, 70.27; H. 7.21.

EXAMPLE 14

Enzymatic Resolution of (±)-Calanolide A

To a magnetically stirred suspension of (±)-Calanolide A, prepared by the method of the present invention, and vinyl butyrate (0.1 mL) in hexane (0.5 mL) at ambient temperature was added 1 mg of lipase PS-13 (Pseudomonas Species) (Sigma Corporations, St. Louis, Mo., USA). The reaction mixture was stirred and monitored by conventional means such as TLC analysis. At 10 days, an additional 1 mg of lipase PS-13 was added. After stirring for a total of 20 days, the reaction was stopped because there was no obvious increase in ester formation. The enzyme was filtered out and the filtrate was concentrated to dryness. The residue was analyzed by HPLC (see Example 13), which showed that 21% of (−)-calanolide A had been converted into its butyrate ester form. The enriched (+)-calanolide A and the butyrate ester of (−)-calanolide A can be easily separated by conventional means such as column chromatography. The enriched (+)-calanolide A may be repeatedly treated with vinyl butyrate and lipase PS-13 as described above so as to obtain high e.e. of (+)-calanolide A.

EXAMPLE 15

In Vitro evaluation of (±)- and (−)-calanolide A

This example illustrates the anti-HIV viral activity of the synthetic (±)-calanolide A and its pure enantiomers, (+)-calanolide A and (−)-calanolide A, were evaluated using the published MTT-tetrazolium method.[20] Retroviral agents, AZT and DDC, were used as controls for comparison purposes.

Figure 1B:
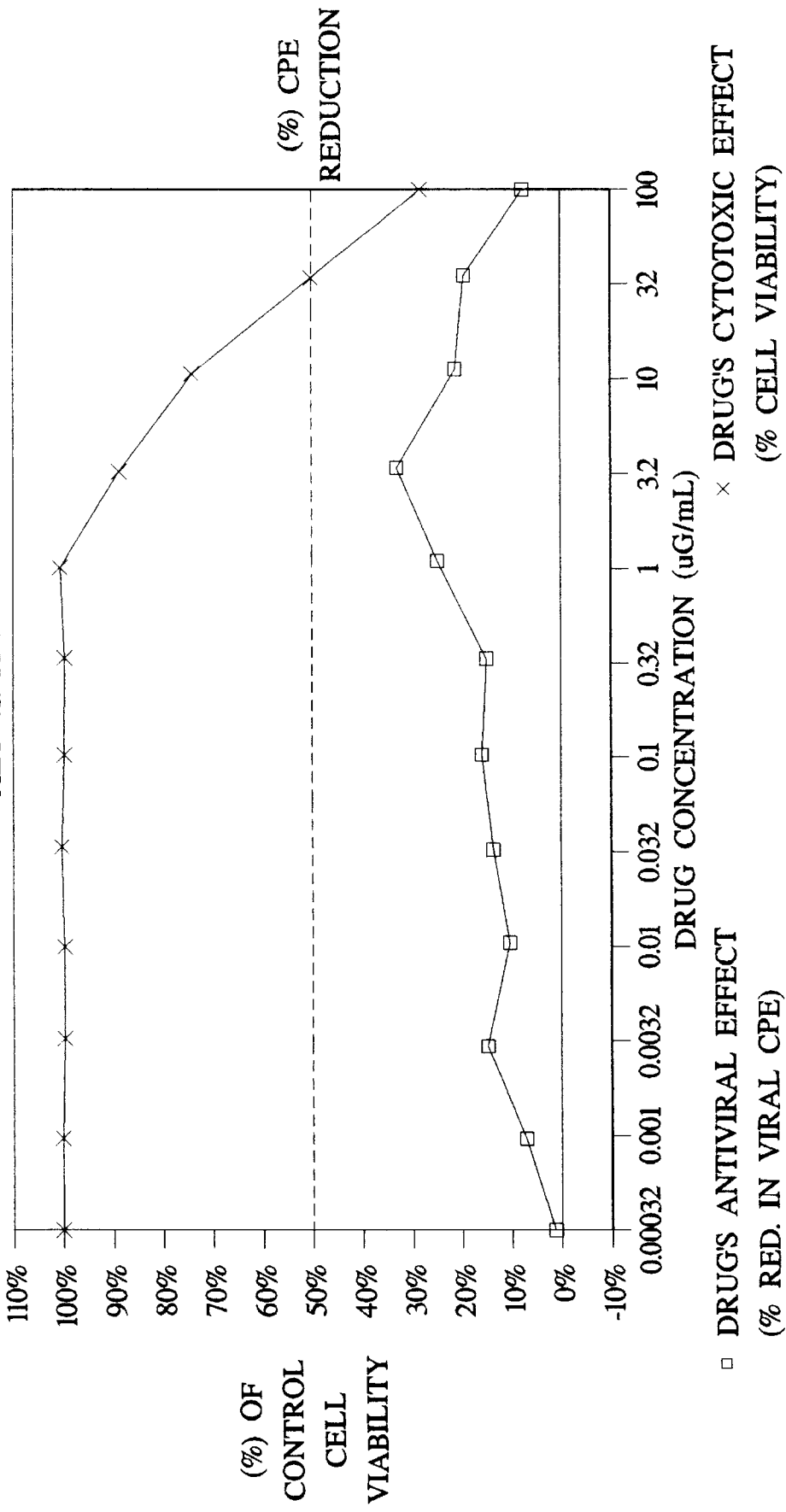
Figure 1C:
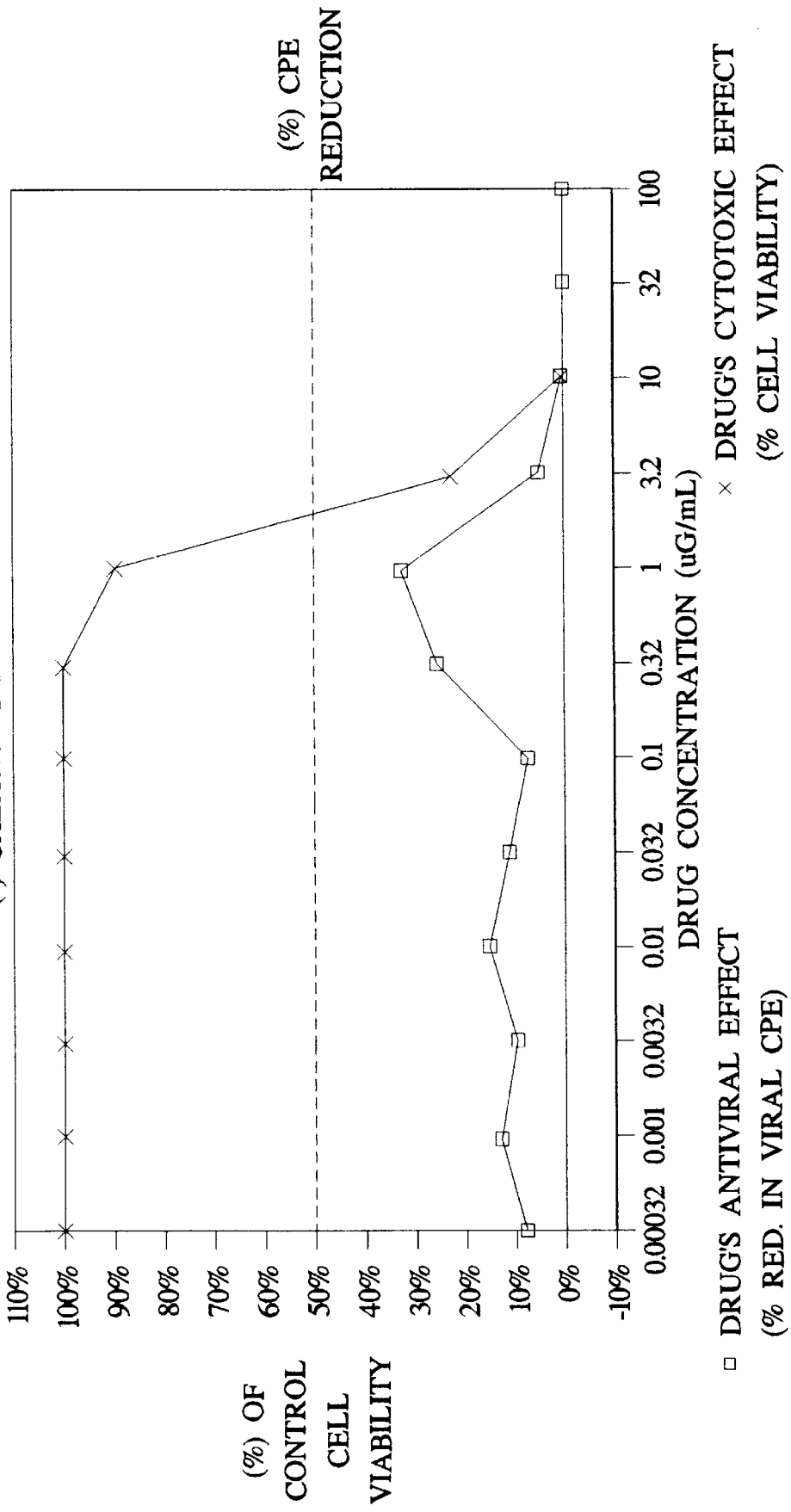
Figure 1D:
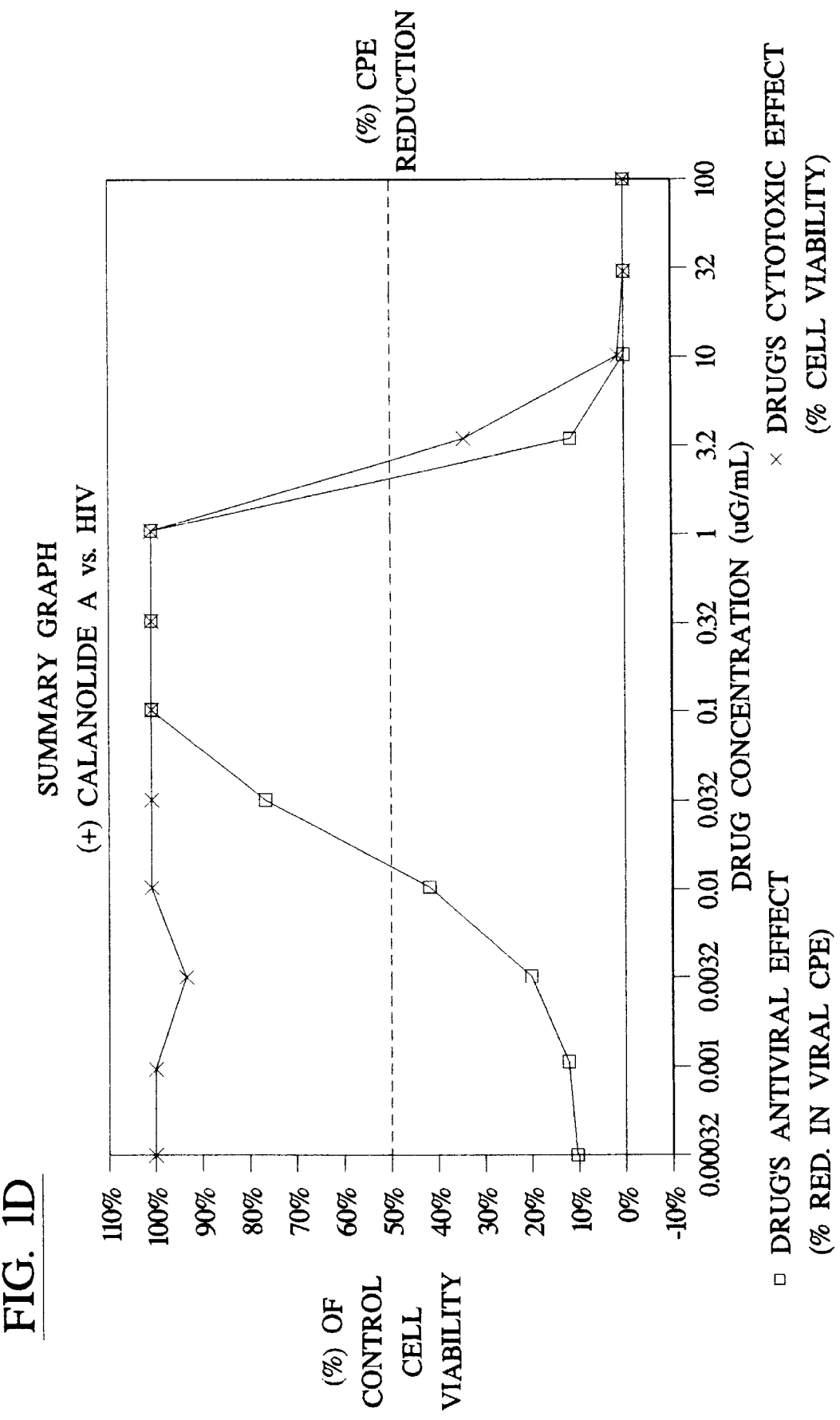
Figure 1E:
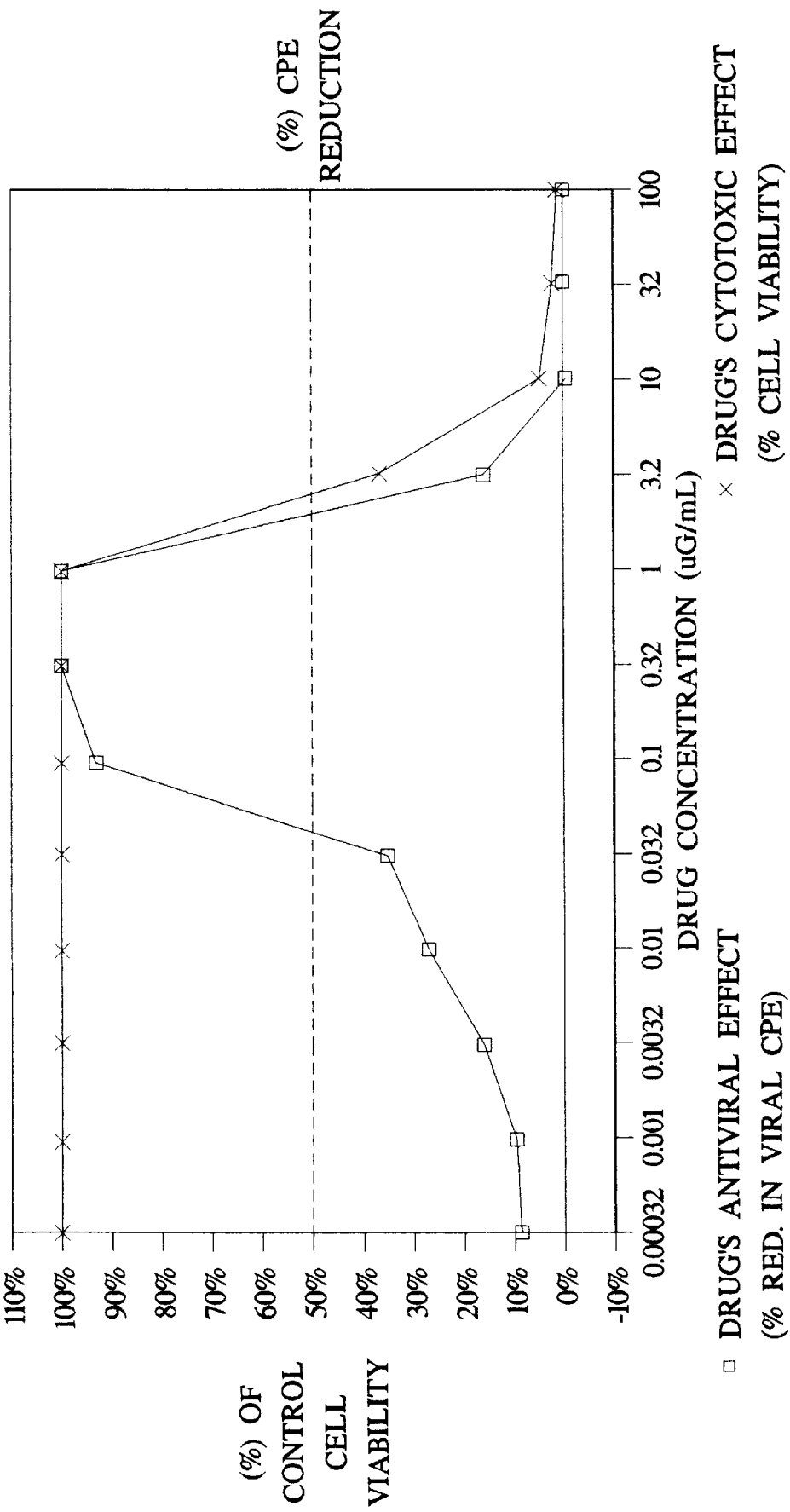

The cells used for screening were the MT-2 and the human T4-lymphoblastoid cell line, CEM-SS, and were grown in RPMI 1640 medium supplemented with 10% fetal (v/v) heat-inactivated fetal calf serum and also containing 100 units/ml penicillin, 100 μg/ml streptomycin, 25 mM HEPES and 20 μg/ml gentamicin. The medium used for dilution of drugs and maintenance of cultures during the assay was the same as above. The HTLV-IIIB and HTLV-RF were propagated in CEM-SS. The appropriate amounts of the pure compounds for anti-HIV evaluations were dissolved in DMSO, then diluted in medium to the desired initial concentration. The concentrations (ug drug/mL medium) employed were 0.0032 ug/mL; 0.001 ug/ml; 0.0032 ug/mL; 0.01 ug/mL; 0.032 ug/mL; 0.1 ug/mL; 0.32 ug/mL; 1 ug/mL; 3.2 ug/mL; 10 ug/mL; 32 ug/mL; and 100 ug/mL. Each dilution was added to plates in the amount of 100 μl/well. Drugs were tested in triplicate wells per dilution with infected cells while in duplicate wells per dilution with uninfected cells for evaluation of cytotoxicity. On day 6 (CEM-SS cells) and day 7 (MT-2 cells) post-infection, the viable cells were measured with a tetrazolium salt, MTT (5 mg/ml), added to the test plates. A solution of 20% SDS in 0.001 N HCl is used to dissolve the MTT formazan produced. The optical density value was a function of the amount of formazan produced which was proportional to the number of viable cells. The percent inhibition of CPE per drug concentration was measured as a test over control and expressed in percent (T/C%). The data is summarized in FIGS. 1(a–e), 2(a–e), 3(a–e), 4(a–d), and 5(a–d).

FIGS. 1(a) to 1(e) illustrate in vitro MTT assay results using an isolate, G9106 HIV viral strain[21], which is AZT-resistant. The data shows that (–)-calanolide A was relatively non-toxic at concentrations of 1 ug/mL but exhibited very little antiviral effect. Moreover, (±)-calanolide A was effective as (+)-calanolide A in reducing viral CPE. As expected, AZT had little to no effect in reducing viral CPE and enhancing cell viability.

Figure 2A:
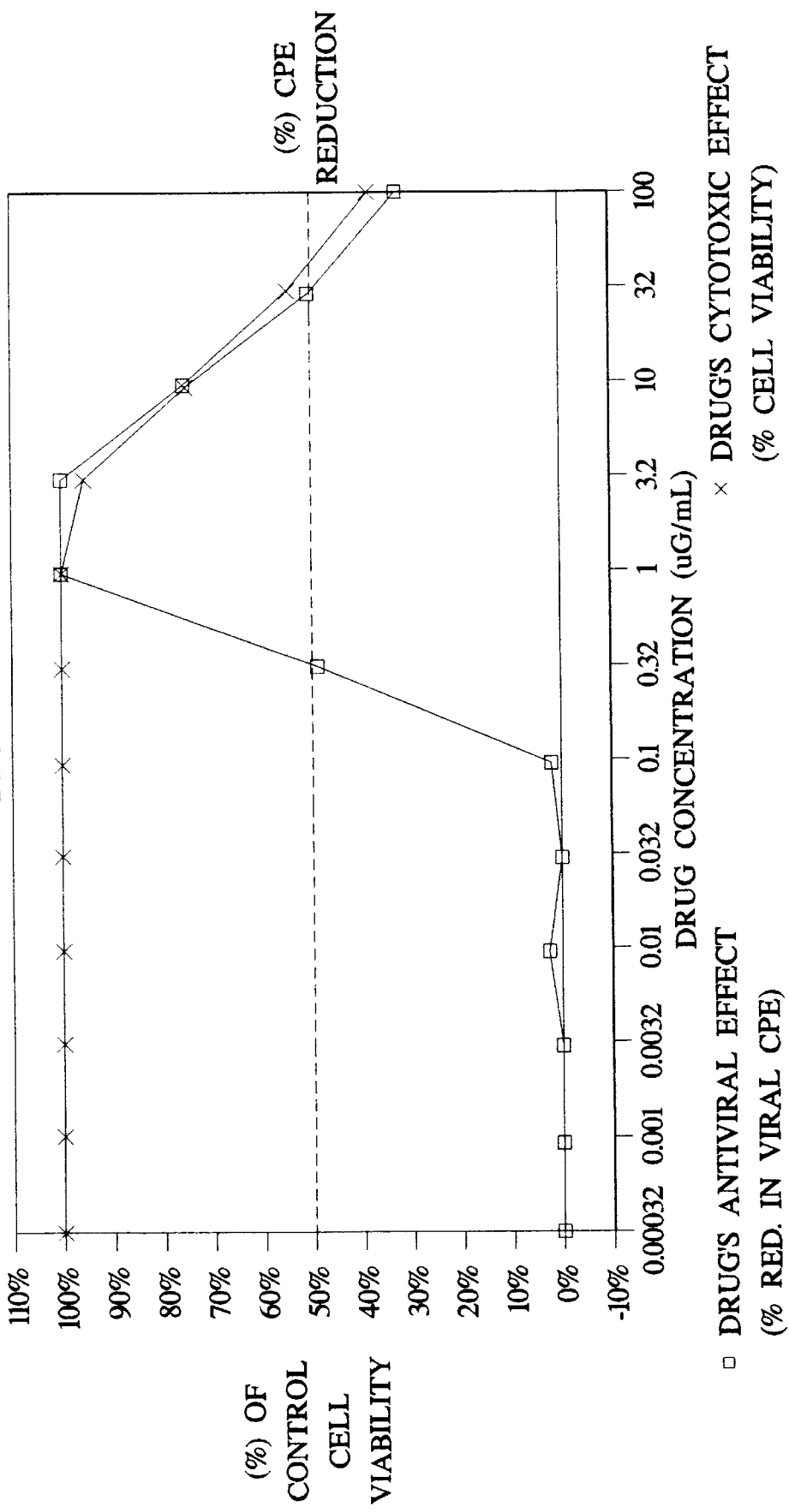
Figure 2B:
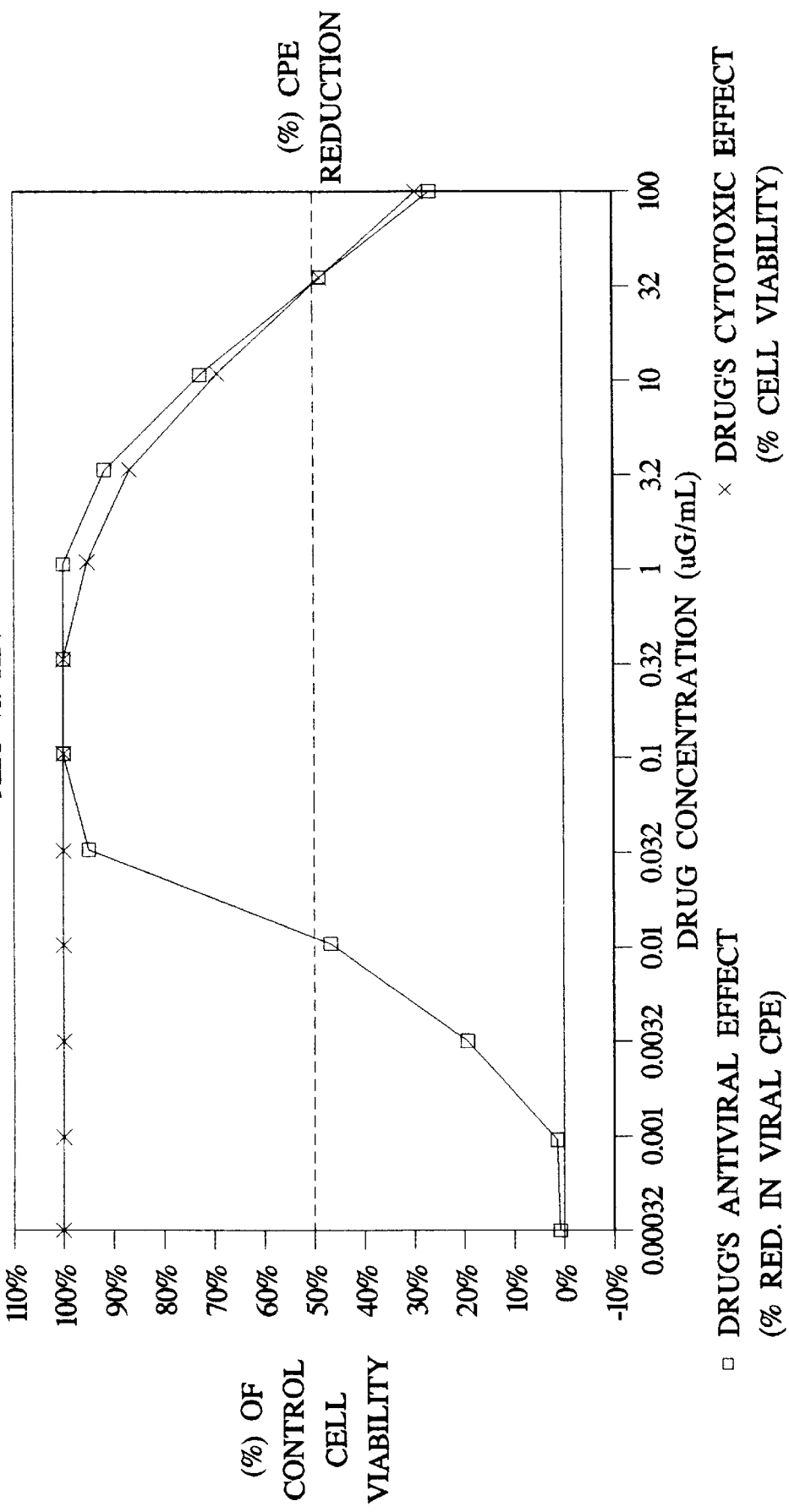
Figure 2D:
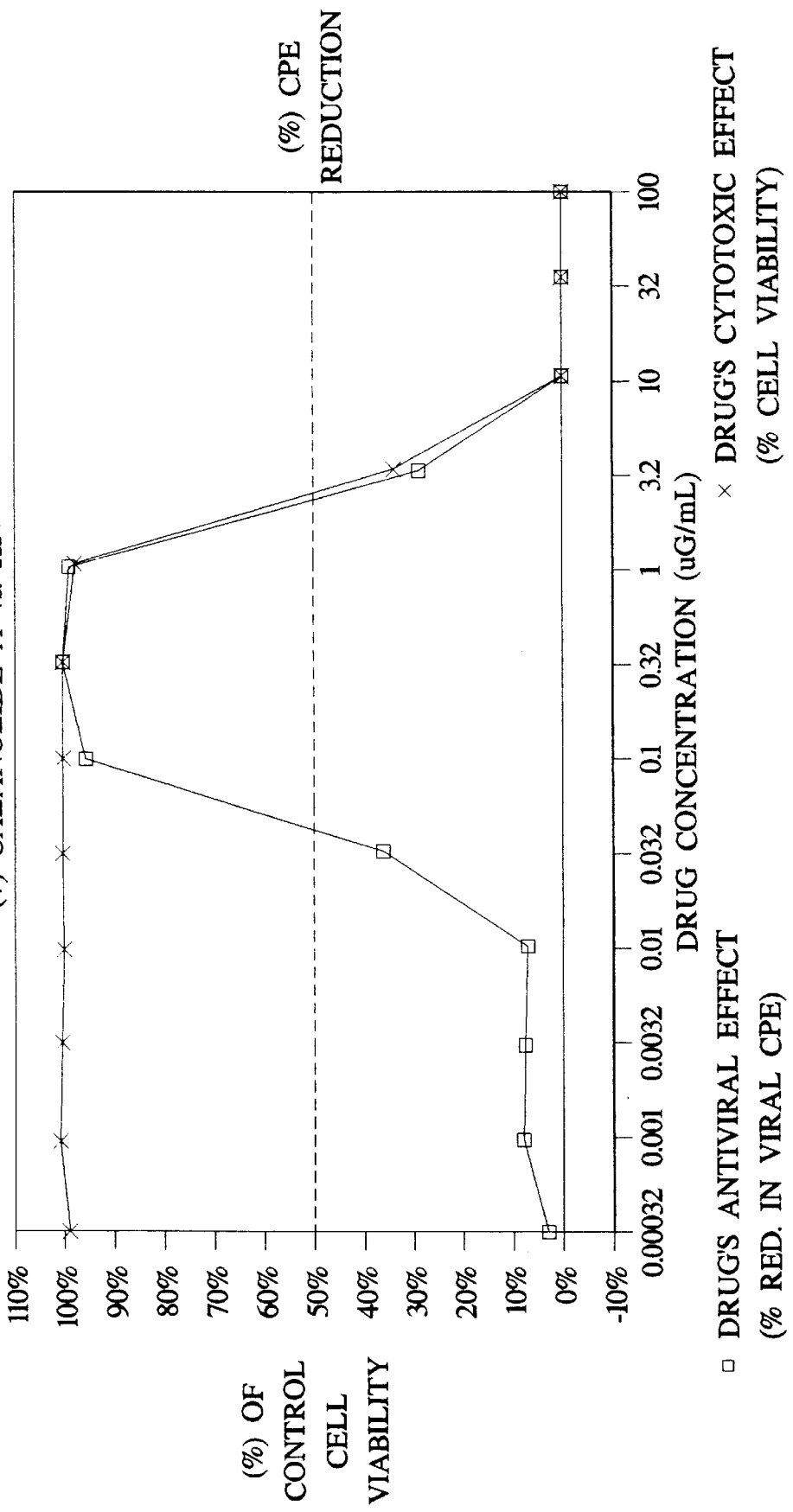
Figure 2E:
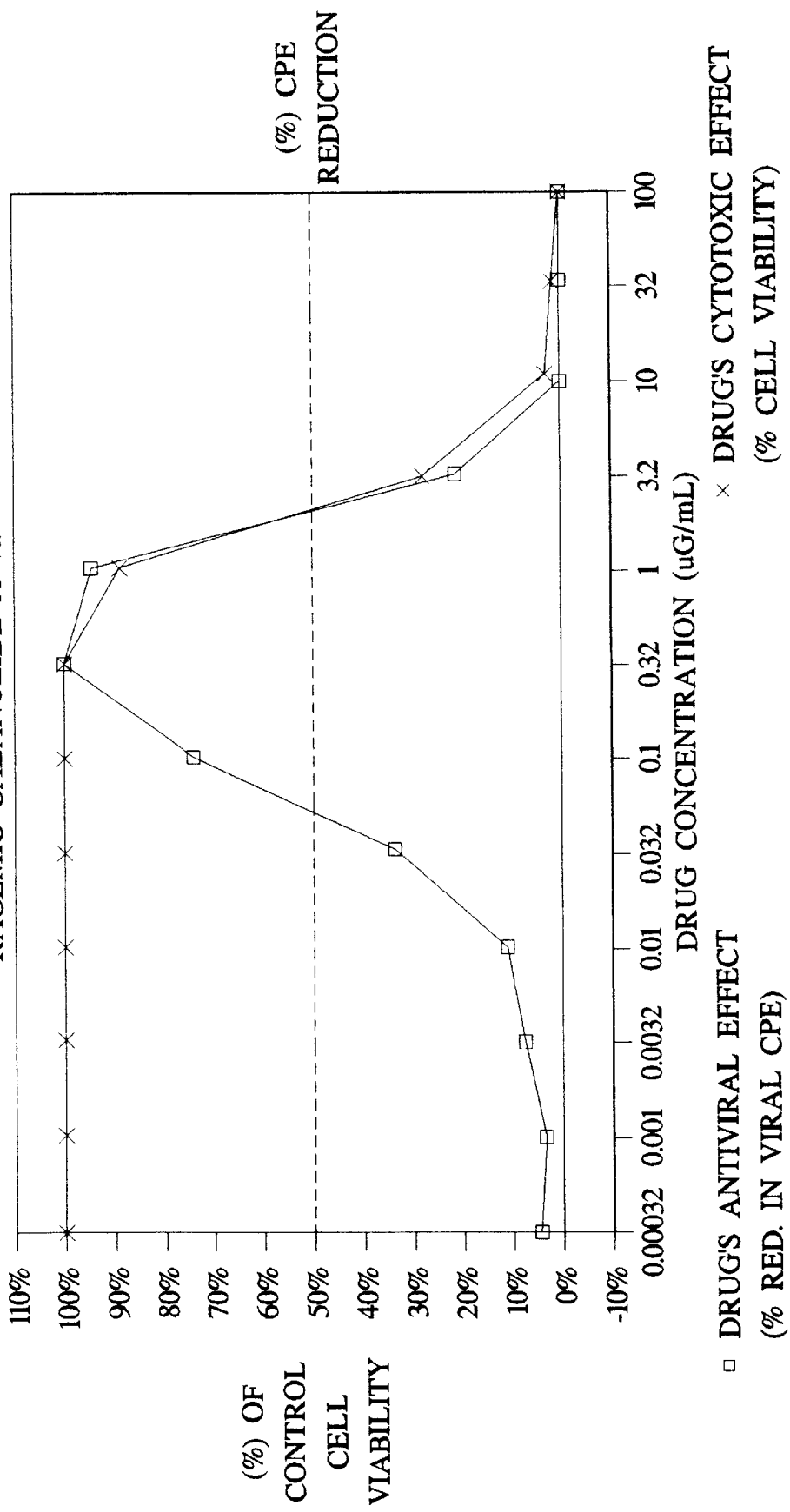

FIGS. 2(a) to 2(e) illustrate in vitro MTT assay results using H112-2 HIV viral strain which was not pretreated with AZT. As expected, the viral strain was sensitive to AZT. The data also showed that (–)-calanolide A was relatively non-toxic at concentrations of 1 ug/mL but exhibited very little antiviral effect. (±)-calanolide A was nearly as effective as (+)-calanolide A in reducing viral CPE.

Figure 3A:
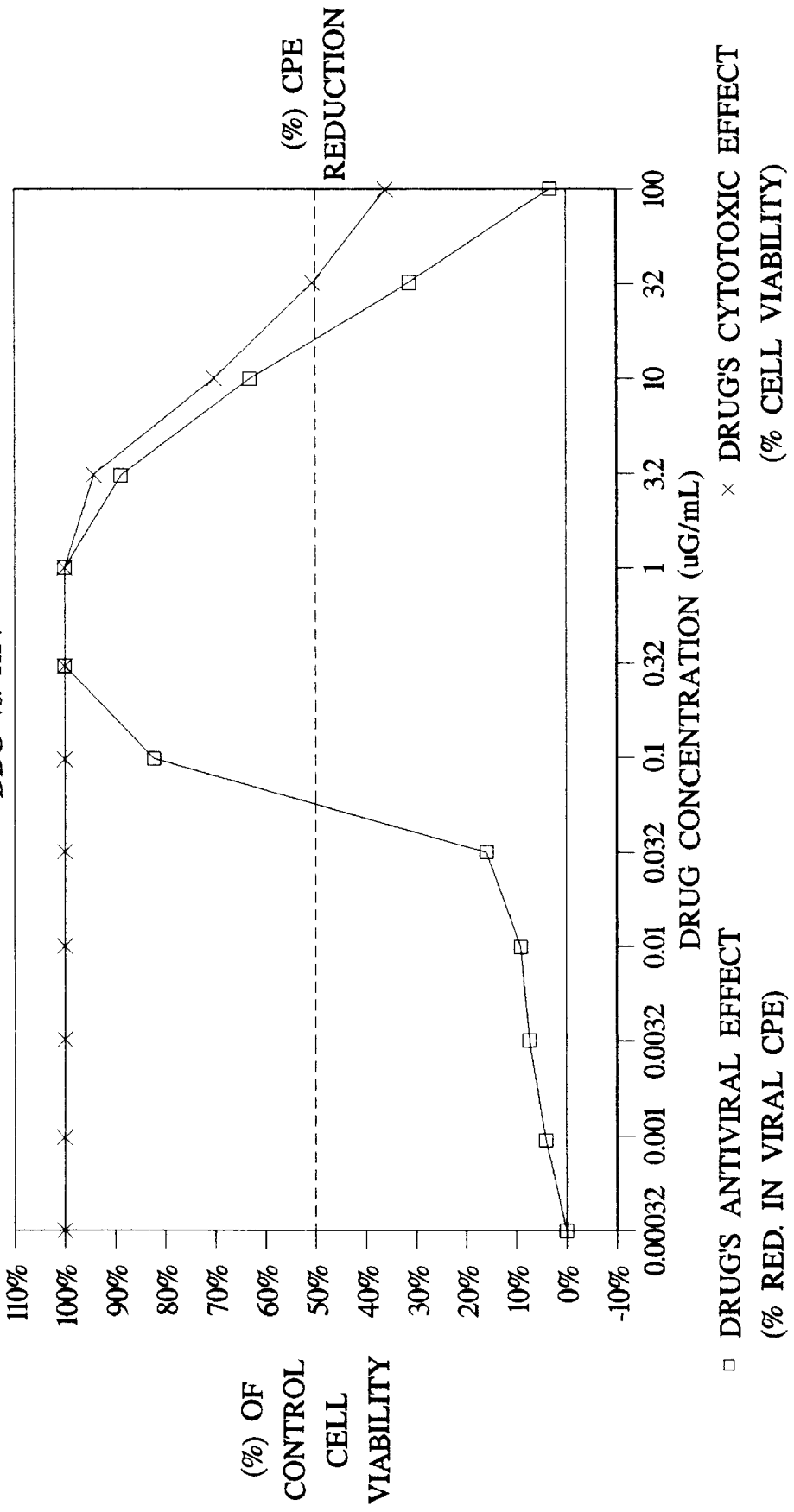
FIGS. 3(a) to 3(e) illustrate in vitro MTT assay results, as described in Example 15, using A-17 HIV viral strain which is resistant to non-nucleoside inhibitors such as TIBO and pyridinone but is sensitive to AZT.
Figure 3B:
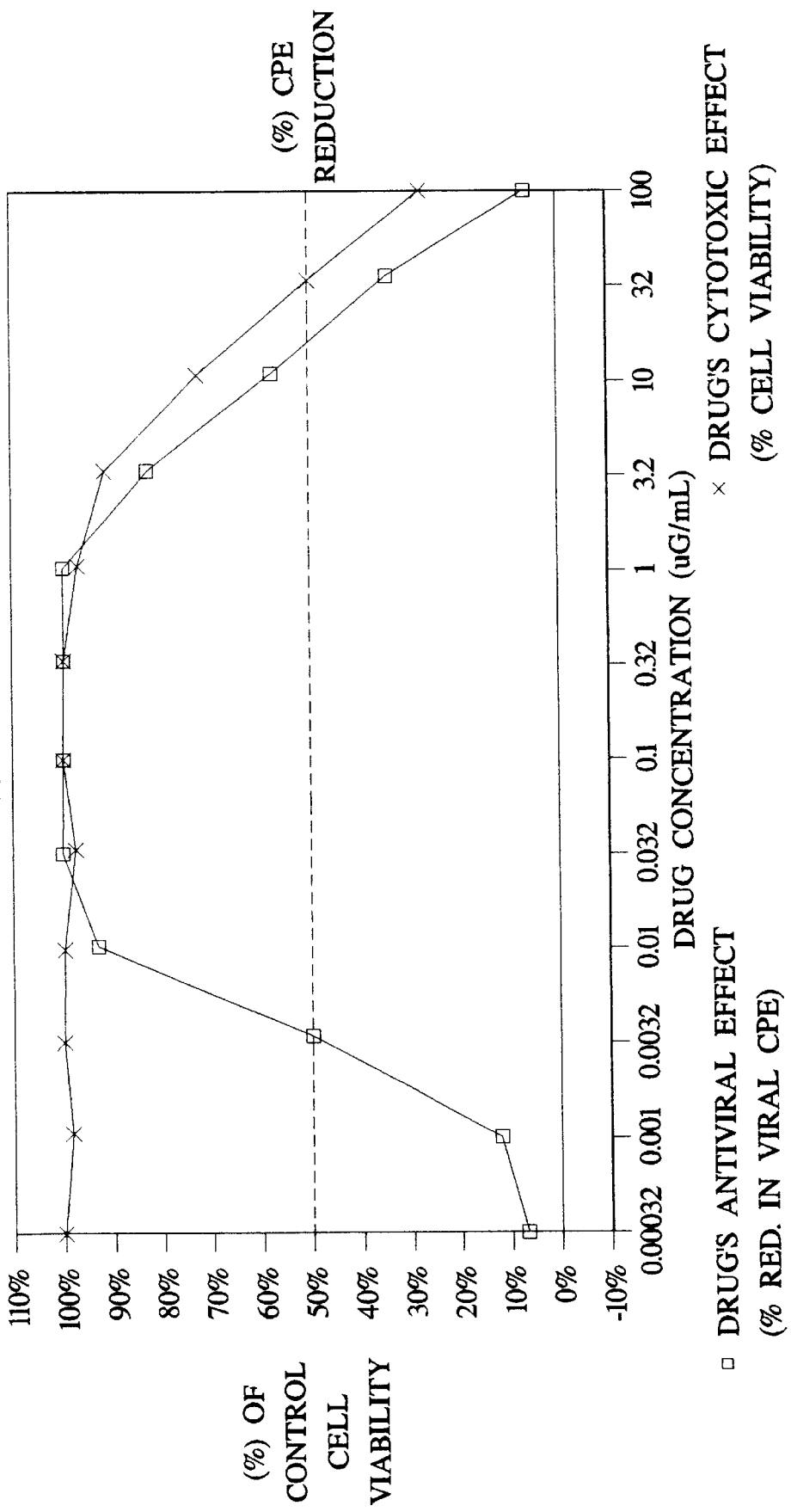
Figure 3C:
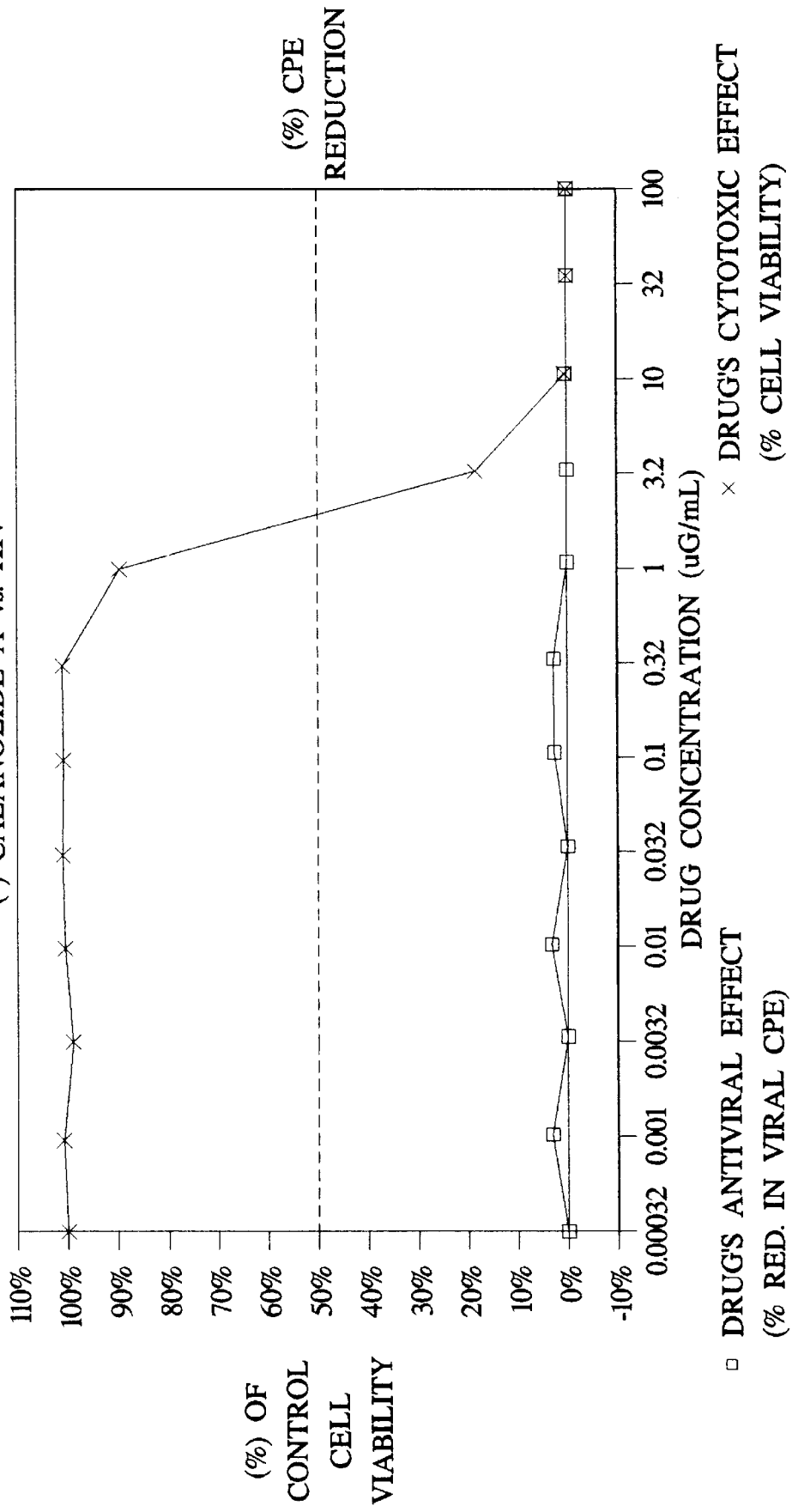
Figure 3D:
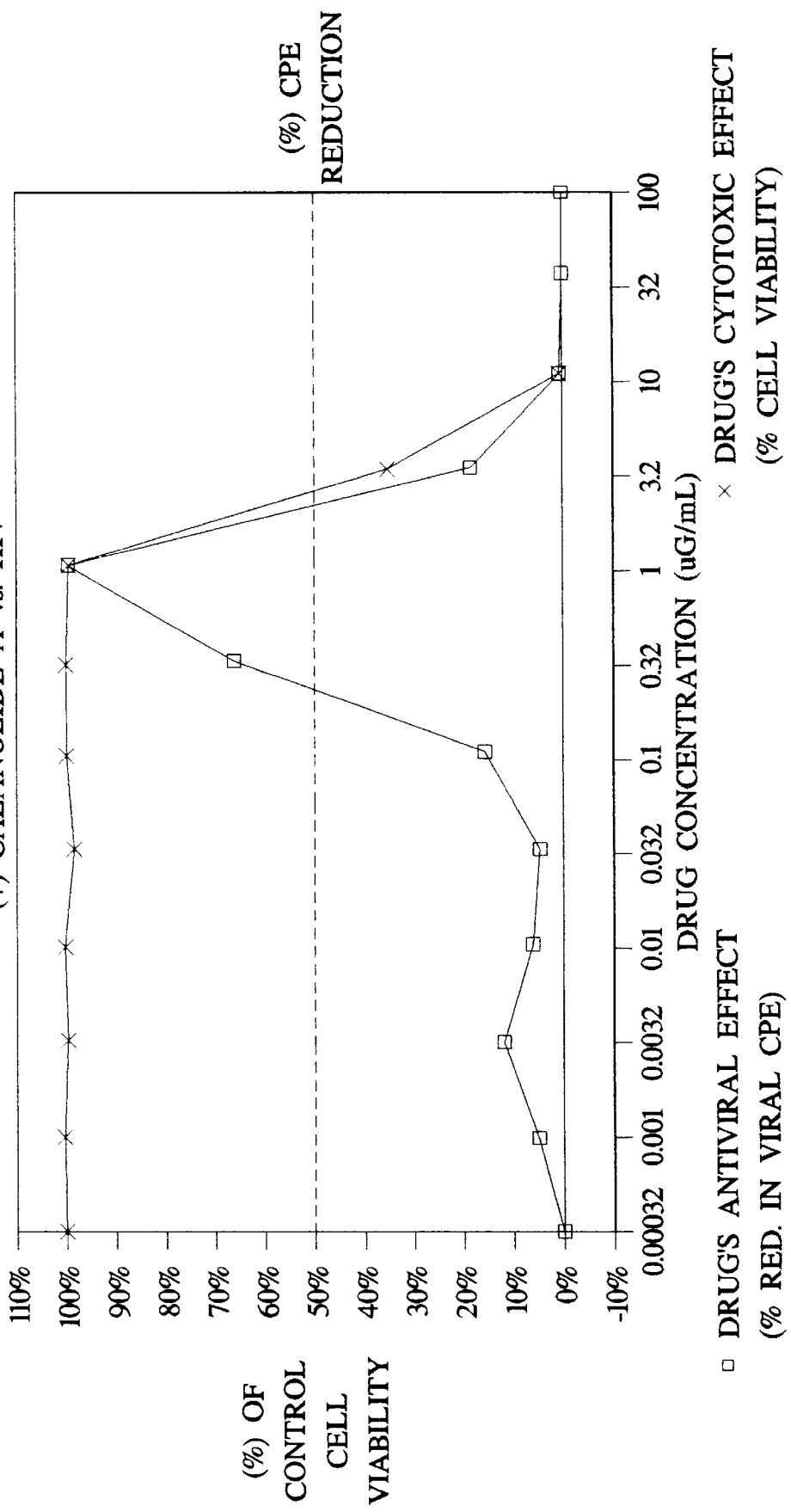
Figure 3E:
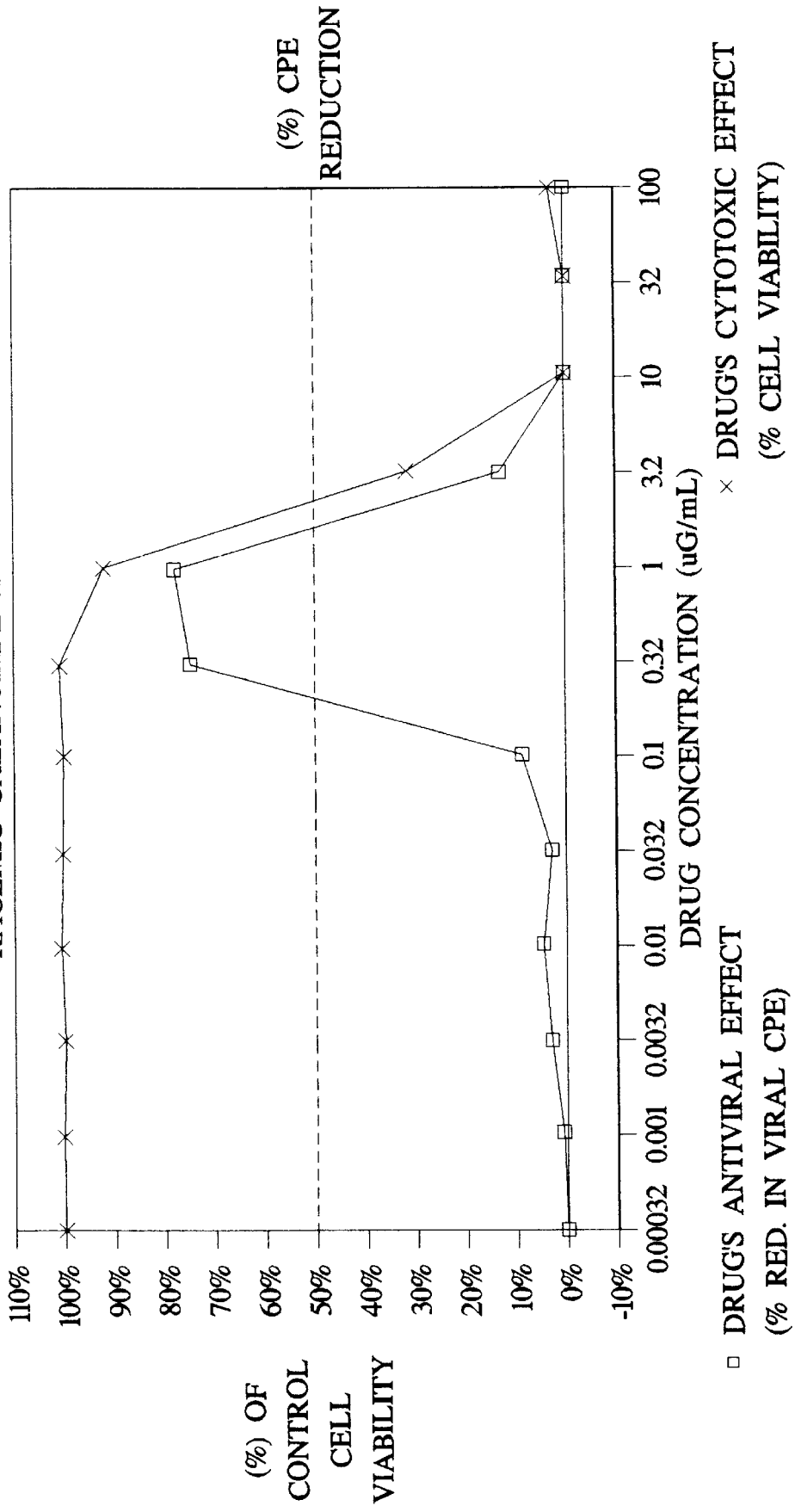

FIGS. 3(a) to 3(e) illustrates in vitro MTT assay results using A-17 HIV viral strain[22] which is resistant to to non-nucleoside inhibitors such as TIBO and pyridinone but is sensitive to AZT. The results here parallel those shown in FIGS. 2(a)–2(e).

Figure 4A:
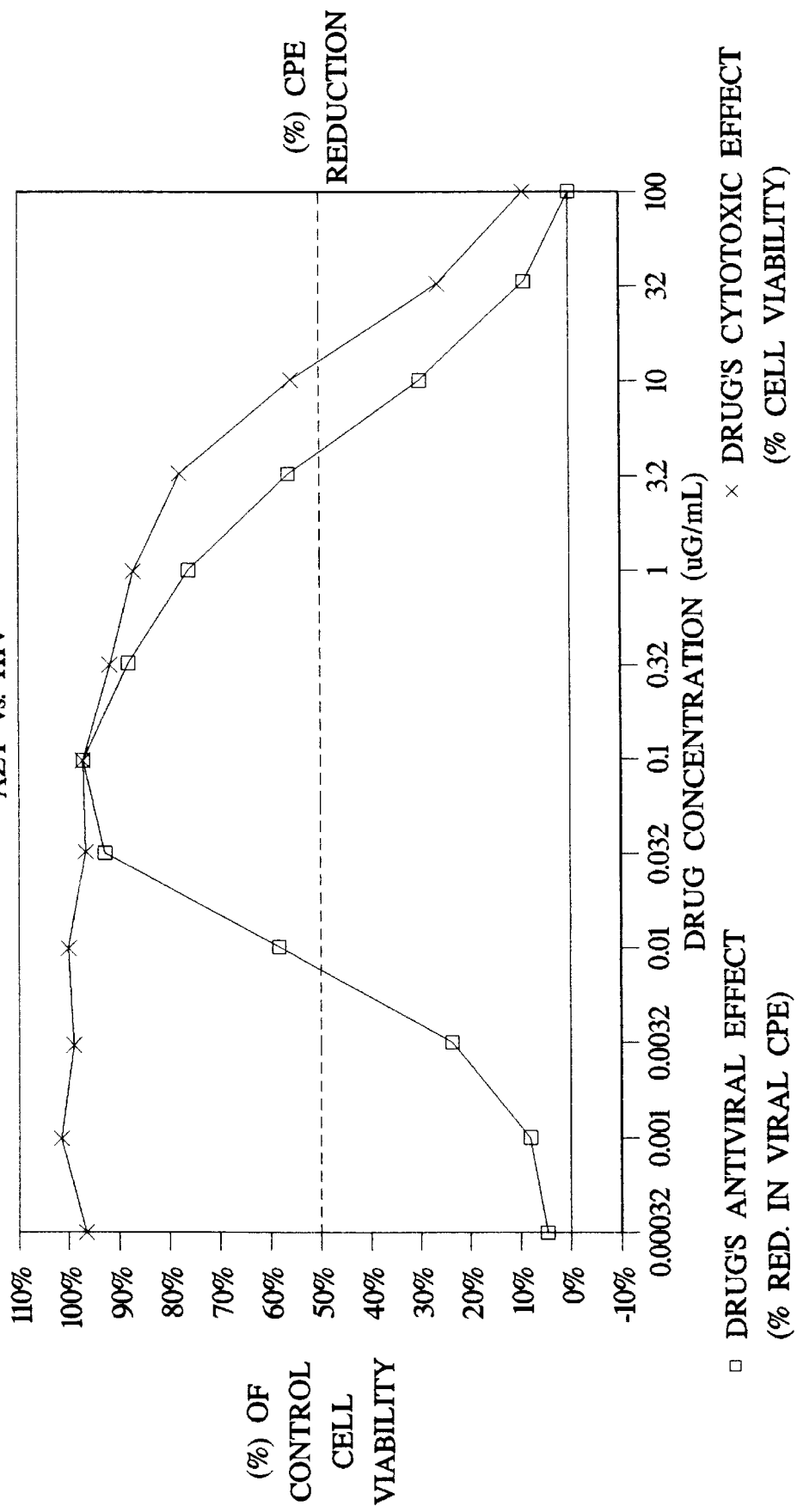
FIGS. 4(a) to 4(d) illustrate in vitro MTT assay results, as described in Example 15, using IIIB cultivated HIV viral strain.
Figure 4B:
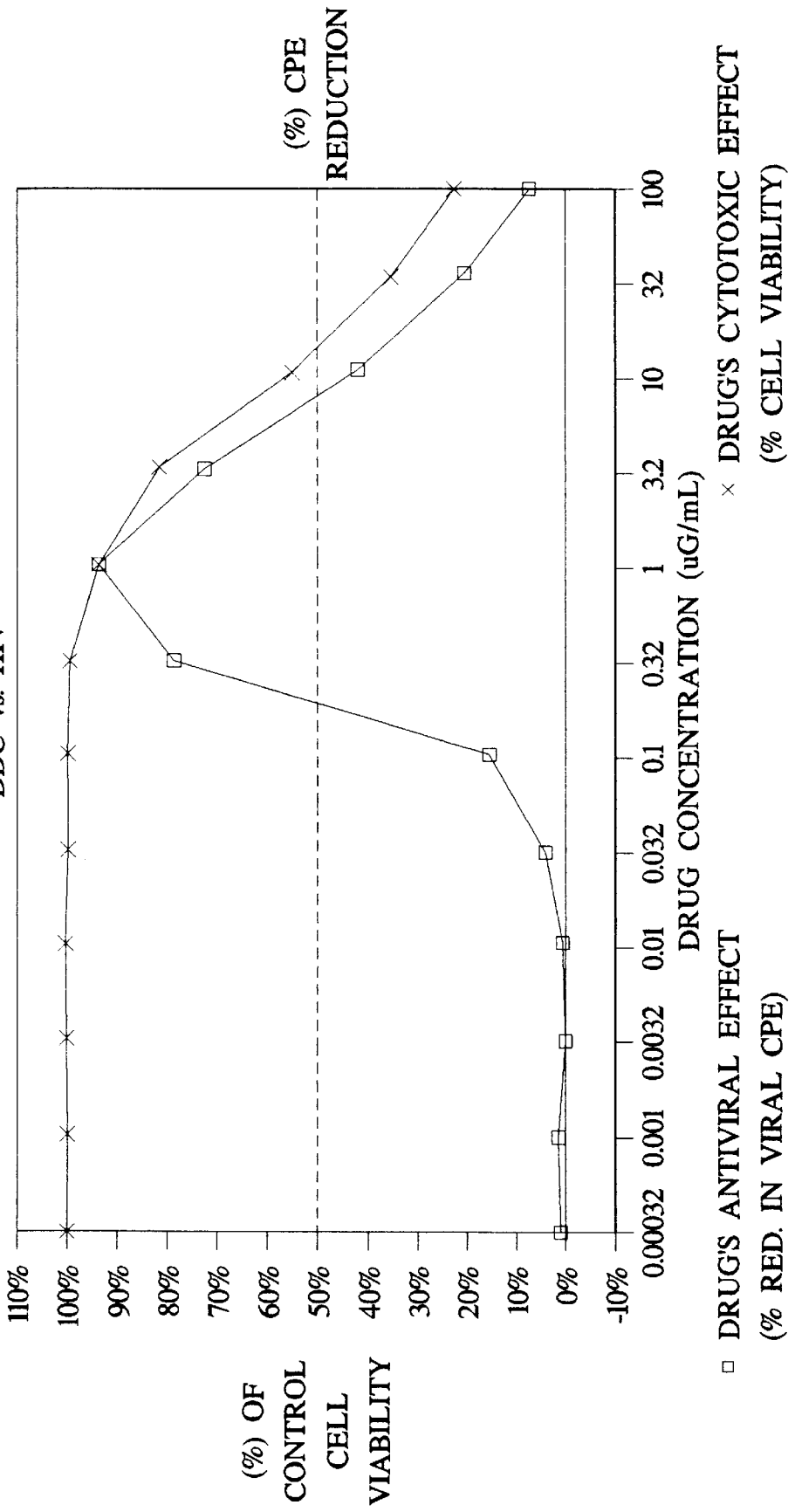
Figure 4C:
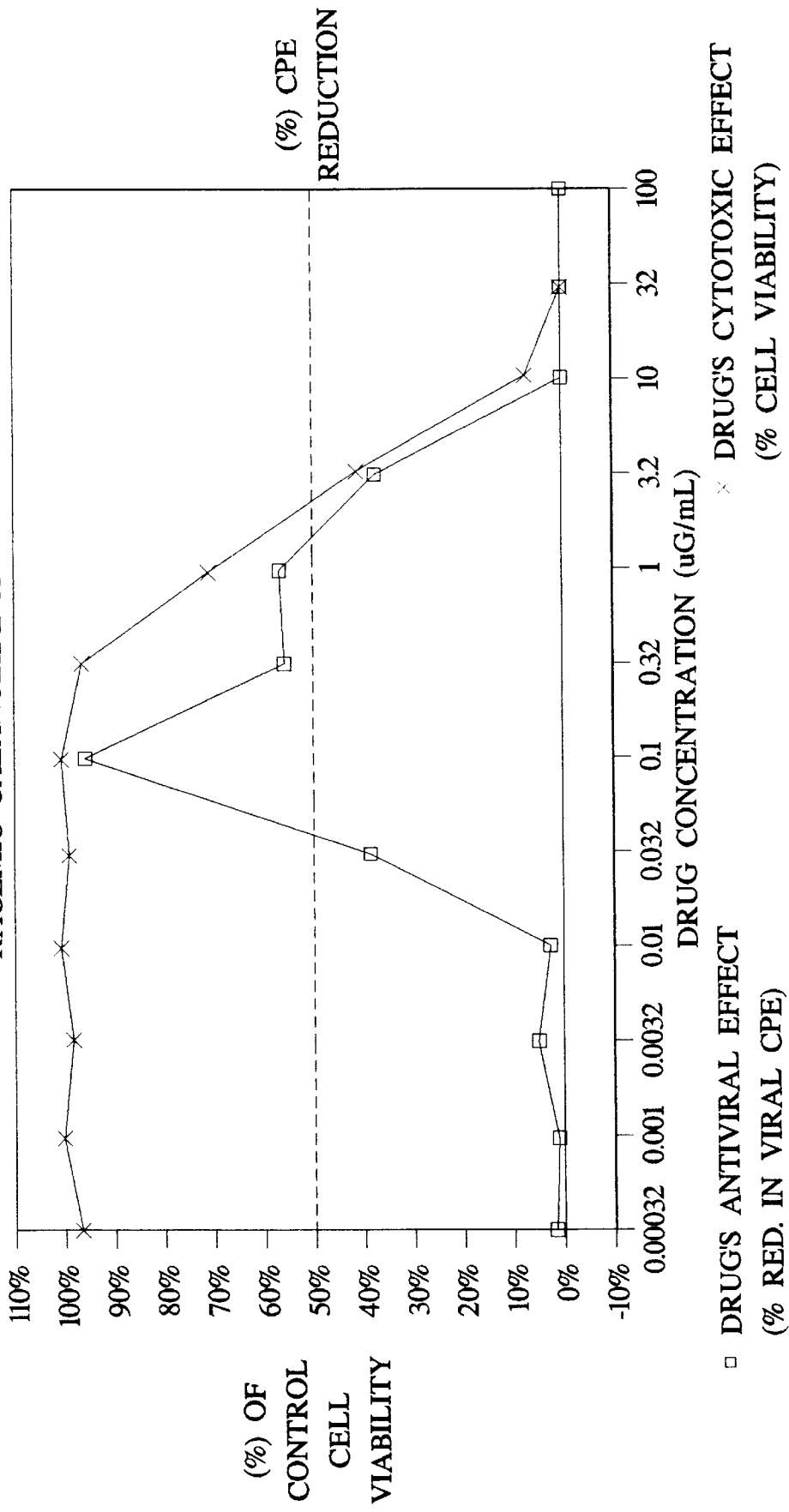
Figure 4D:
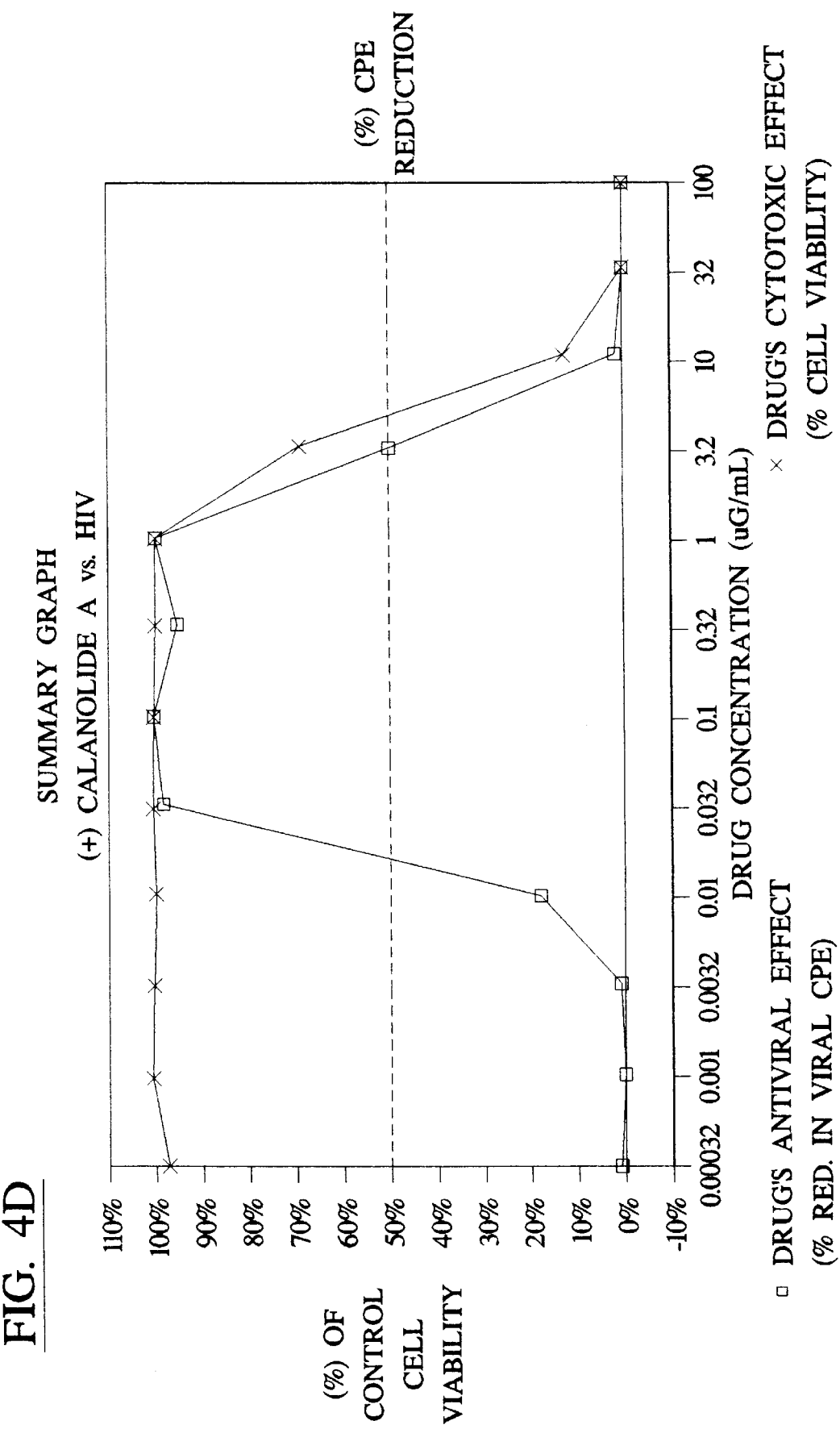
Figure 5A:
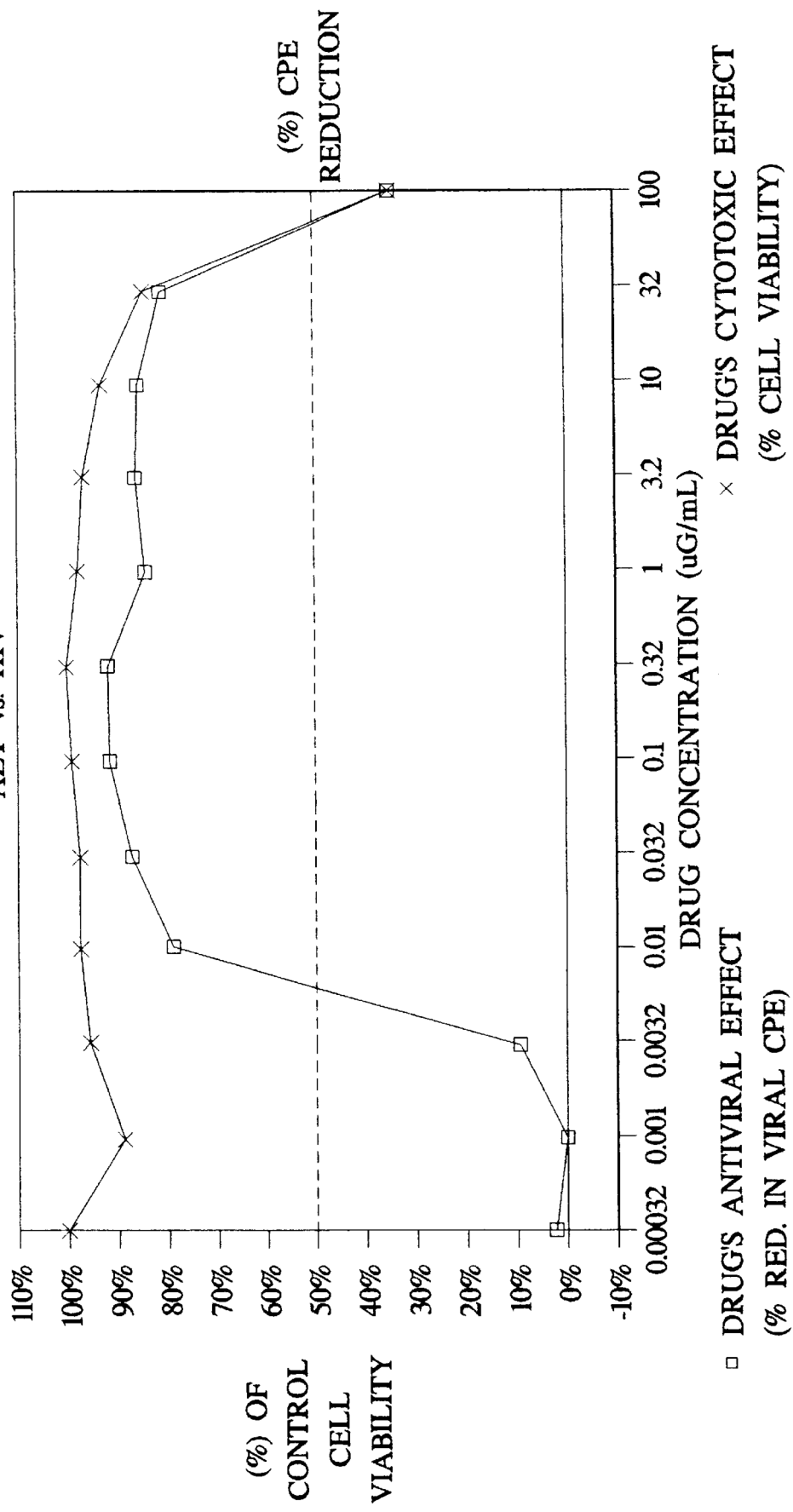
FIGS. 5(a) to 5(d) illustrate in vitro MTT assay results, as described in Example 15, using RF cultivated HIV viral strain.
Figure 5B:
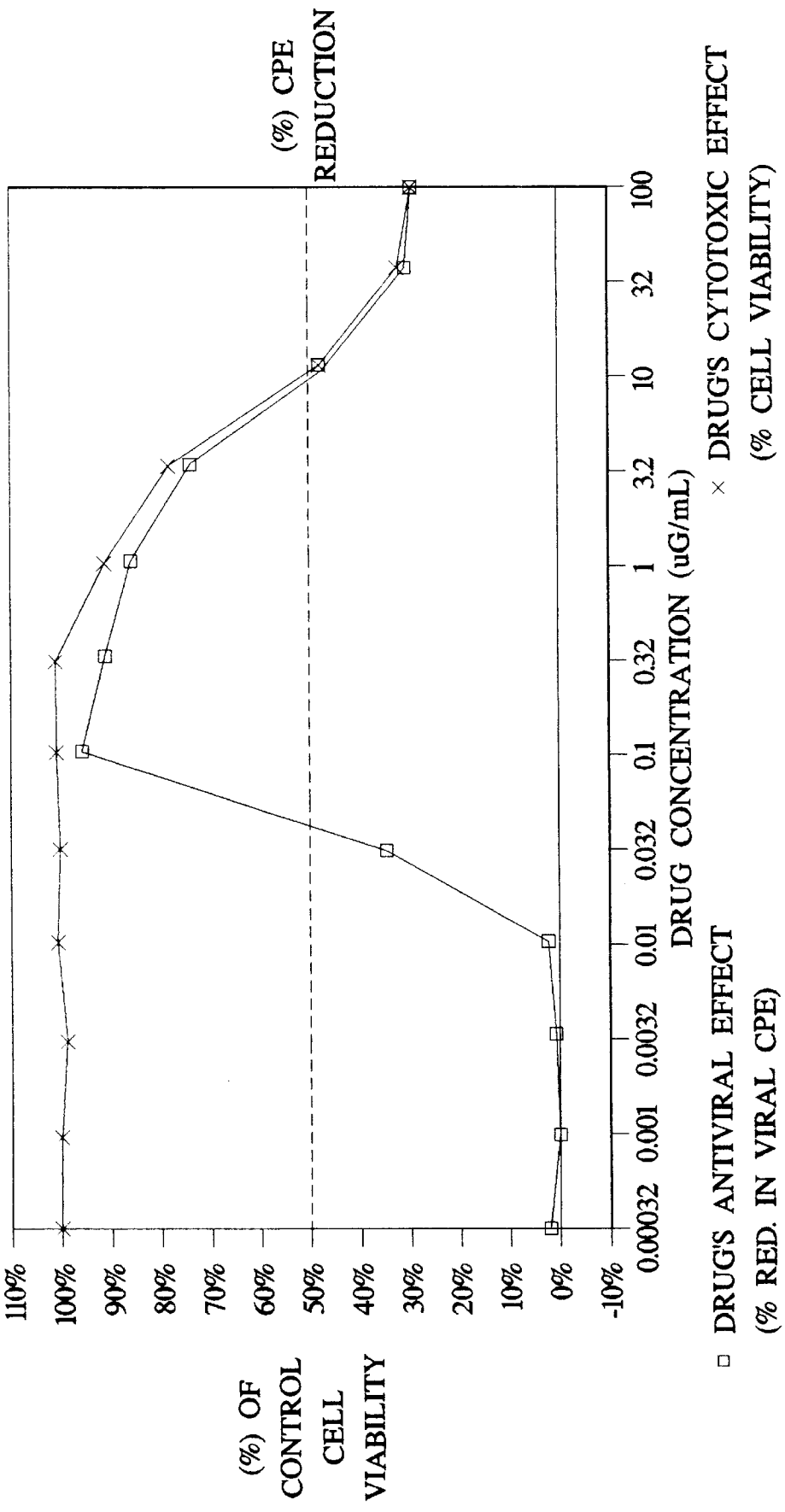
Figure 5C:
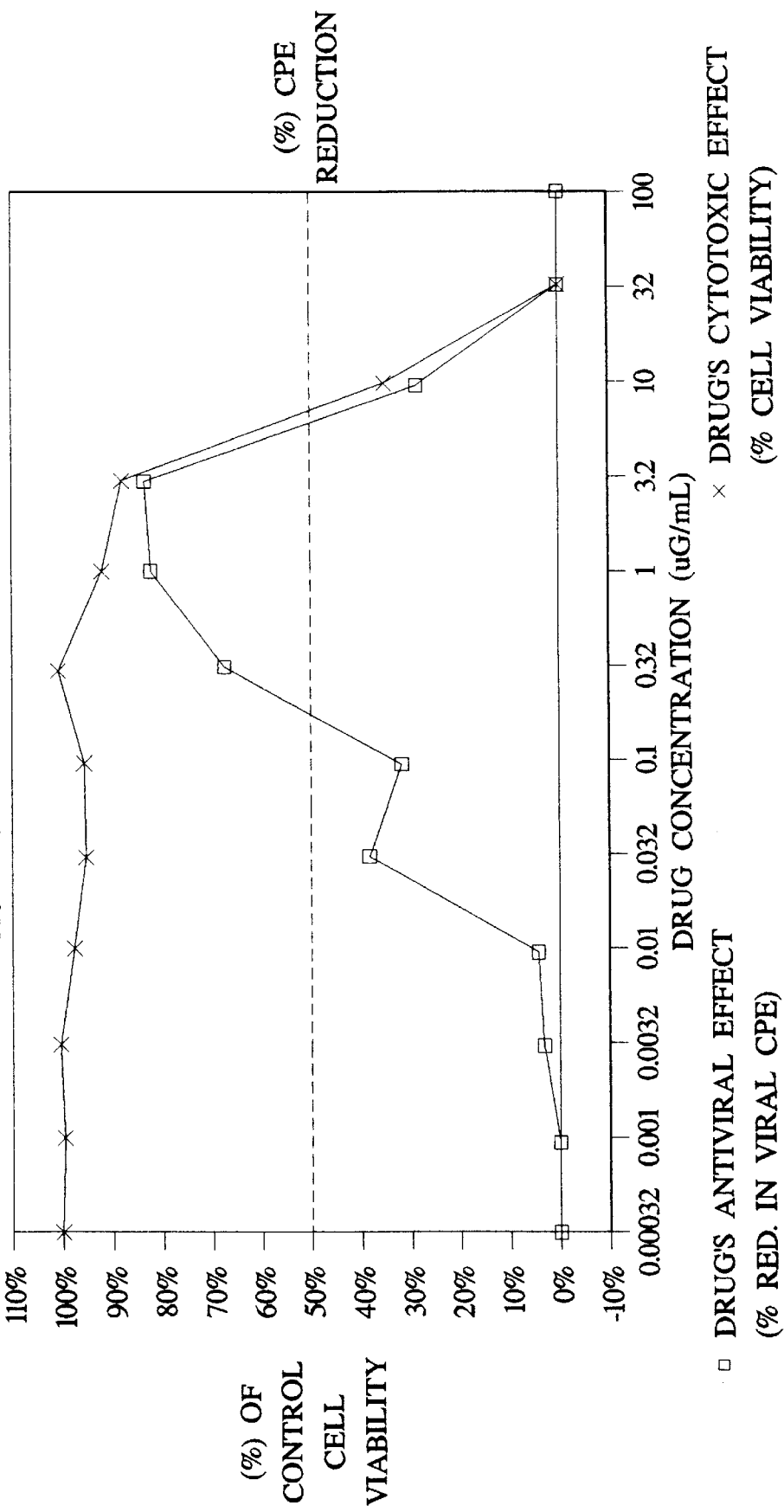
Figure 5D:
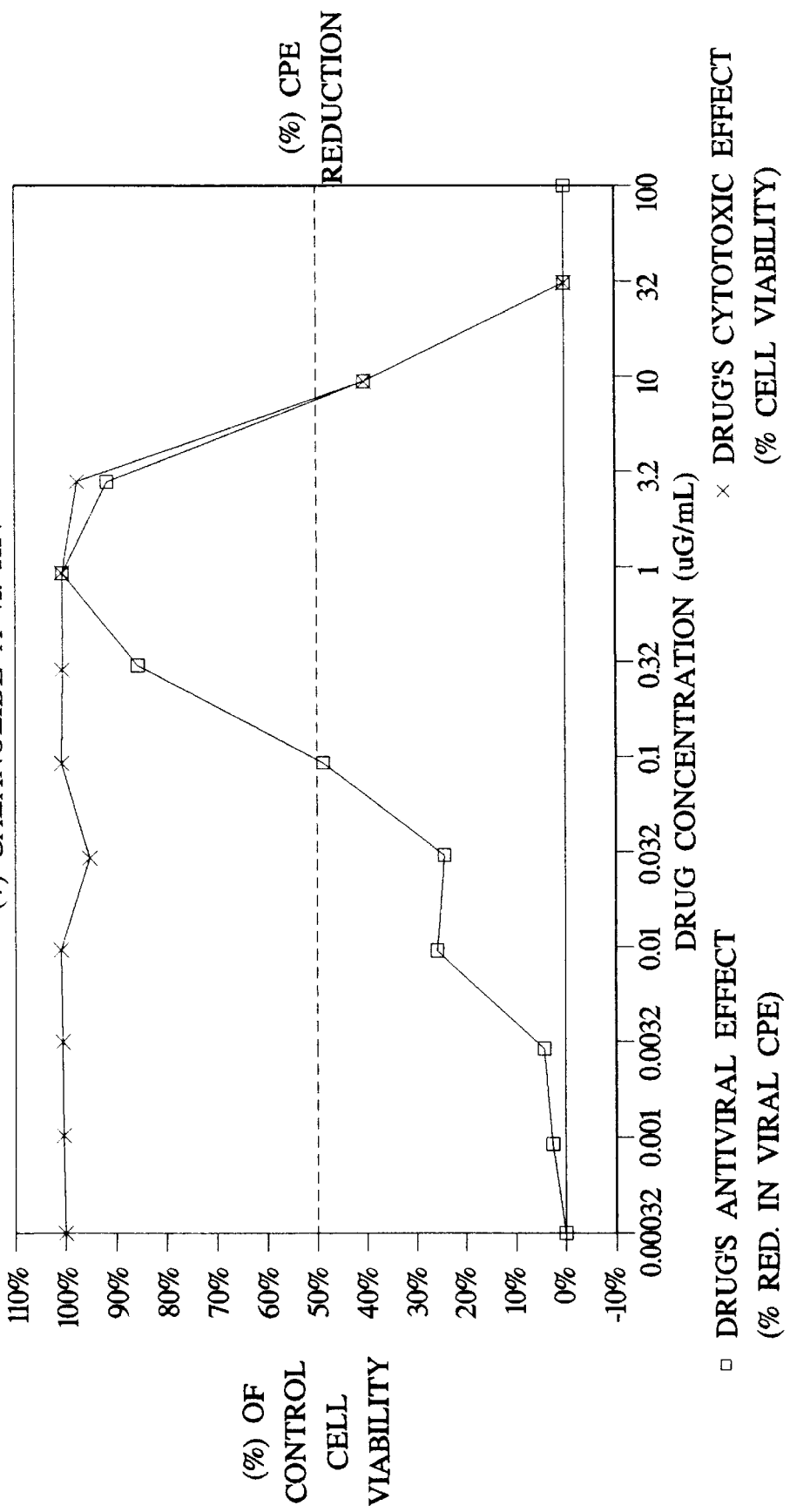

FIGS. 4(a)–(d) and 5(a)–(d) illustrate in vitro MTT assay results using lab cultivated HIV viral strains IIIB and RF, respectively. The results here also parallel those shown in FIGS. 2(a)–2(e).

REFERENCES

1a. Brookmeyer, R., Reconstruction and Future Trends of the AIDS Epidemic in the United States, *Science*, 1991, 253, 37–42.

b. Brain, M. M.; Heyward, W. L.; Curran, J. W., The Global Epidemiology of HIV Infection and AIDS, *Annu. Rev. Microbiol.*, 1990, 44, 555–577.

2a. Weislow, O. S.; Kiser, R.; Fine, D. L.: Bader, J. Shoemaker, R. H.; Boyd, M. R., New Soluble-formazan Assay for HIV-1 Cytopathic Effects: Application to High-Flux Screening of Synthetic and Natural Products of AIDS-Antiviral Activity. *J. Natl. Cancer Inst.*, 1989, 81, 577–586.

b. Mitsuya, H.; Yarchoan, R.; Broder, S., Molecular Targets for AIDS Therapy. *Science*, 1990, 249, 1533–1544.

c. Petteway, S. R., Jr.; Lambert, D. M.; Metcalf, B. W., The Chronically Infected Cells: A Target for the Treatment of HIV Infection and AIDS. *Trends Pharmacol. Sci.*, 1991, 12, 28–34.

d. Richman, D. D., Antiviral Therapy of HIV Infection, *Annu. Rev. Med.*, 1991, 42, 69–90.

e. Haden, J.W., Immunotherapy of Human Immunodeficiency Virus Infection. *Trends Pharmacol Sci.*, 1991, 12, 107–111.

f. Huff, J. R., HIV Protease: A Novel Chemotherapeutic Target for AIDS. *J. Med. Chem.*, 1991, 34, 2305–2314.

g. De Clercq, E., HIV Inhibitors Targeted at the Reverse Transcriptase. *AIDS Research and Human Retroviruses*, 1992, 8, 119–134.

3. Kashman, Y.; Gustafson, K. R.; Fuller, R. W.; Cardellina, J. H., II; McMahon; J. B.; Currens, M. J.; Buckheit, R. W., Jr.; Hughes, S. H.; Cragg, G. M.; Boyd, M. R., The Calanolides, a Novel HIV-Inhibitory Class of Coumarin Derivatives from the Tropical Rainforest Tree, *Calophyllum lanigerum. J. Med. Chem.* 1992, 35, 2735–2743.

4. Boyd, M. R., National Cancer Institute, Personal Communication.

5. Chenera, B.; West, M. L.; Finkelstein, J. A.; Dreyer, G. B. , Total Synthesis of (±)-Calanolide A, a Non-Nucleoside Inhibitor of HIV-1 Reverse Transcriptase. *J. Org. Chem.* 1993, 58, 5605–5606.

6. Sethna, S.; Phadke, R., The Pechmann Reaction. *Organic Reactions*, 1953, 7, 1–58 and references cited therein.

7. Crombie, L.; Jones, R. C. F.; Palmer, C. J., Synthesis of the Mammea Coumarin. Part 1. The Coumarin of the Mammea A, B, and C Series. *J. Chem. Soc.*, Perkin Trans. 1, 1987, 317–331.

8. Barton, D. H. R.; Donnelly, D. M. X.; Finet, J. P.; Guiry, P. J., Total synthesis of Isorobustin. *Tetrahedron Lett.* 1990, 31, 7449–7452.

9. Kovacs, T. S.; Zarandy, M. S.; Erdohelyi, A., Cyclization of the Enol Esters of o-Acyloxyphenyl Alkyl Ketones, IV. A Kenetic Study of the Steps of the Kostanecki-Robinson Reaction. *Helv. Chim. Acta*, 1969, 52, 2636–2641.

10. Fung, N. Y. M.; de Mayo, P.; Schauble, J. H.; Weedon, A. C, Reduction by Tributyltin Hybride of Carbonyl Compounds Absorbed on Silica Gel: Selective Reduction of Aldehydes, *J. org. Chem.* 1978, 43, 3977–3979.

11. Hughes, D. L., The Mitsunobu Reaction. *Organic Reaction*, 1992, 42, 335–656 and references cited therein.

12. Gemal, A. L.; Luche, J. L., Lanthanoids in Organic Synthesis. 6. The Reduction of α-Enones by Sodium Borohydride in the Presence of Lanthanoid Chlorides: Synthetic and Mechanistic Aspects. *J. Am. Chem. Soc.*, 1981, 103, 5454–5459.

13. Very recently, a similar work has been published in the literature; Cardellina, J. H., II; Bokesch, H. R.; McKee, T. C.; Boyd, M. R., Resolution and Comparative Anti-HIV Evaluation of the Enantiomers of Calanolides A and B. *Bioorg. Med. Chem. Lett.* 1995, 5, 1011–1014.

14. Deshpande, P. P., Tagliaferri, F.; Victory, S. F.; Yan, S.; Baker, D. C., Synthesis of Optically Active Calanolides A and B. *J. Org. Chem.* 1995, 60, 2964–2965.

15. For a review, see Nielsen, A. T.; Houlihan, W. J., The aldol Condensation. *Org. React.* 1968, 16, 1–438.

16. For reviews, see:

(a) Mukaiyama, T., The Directed Aldol Reaction. *Org. React.* 1982, 28, 203–331.

(b) Reetz, M. T., Chelation or Non-Chelation Control in Addition Reactions of Chiral α- and β-Alkoxy Carbonyl Compounds, *Angew. Chem. Int. Ed.* Eng. 1984, 23, 556–569.

(c) Shibata, I.; Baba, A., Organotin Enolates in Organic Synthesis. *Org. Prep. Proc. Int.* 1994, 26, 85–100.

17. For a review on chiral titanium complexes, see Duthaler, R. O.; Hafner, A., Chiral Titanium Complexes for Enantioselective Addition of Nucleophiles to Carbonyl Groups. *Chem. Rev.*, 1992, 92, 807–832 and reference cited therein.

18. For a review on chiral boron complexes, see Paterson, L.; Goodman, J. M.; M., Aldol Reactions in Polypropionate Synthesis: High π-Face Selectivity of Enol Borinates from α-Chiral Methyl and Ethyl Ketones under Substrate Control. *Tetrahedron Lett.* 1989, 30, 7121–7124 and references cited therein.

19. Tsunoda, T.; Yamamiya, Y.; Kawamura, Y.; Ito, S., Mitsunobu Acylation of Sterically Congested Secondary Alcohols by N,N,N[1], N[1]-Tetramethylazodicarboxamide-Tributylphosphine Reagents. *Tetrahedron Lett.* 1995, 36, 2529–2530.

20. Gulakowski, R. J.; McMahon, J. B.; Staley, P. G.; Moran, R. A.; Boyd, M. R., A Semiautomated Multiparameter Approach for Anti-HIV Drug Screening, *J. Virol. Methods*, 1991, 33, 87–100.

21. Larder, B. A.; Darby, G.; Richman, D. D., HIV with reduced Sensitivity to Zidovudine (AZT) isolated during Prolonged Therapy. *Science*, 1989, 243, 1731–1734.

22. Nunberg, J. H.; Schleif, W. A.; Boots, E. J.; O'Brien, J. A.; Quintero, J. C.; Hoffman, J. M.; Emini, E. A.; Goldman, M. E., Viral Resistance to Human Immunodeficiency Virus Type 1-specific Pyridinone Reverse Transriptase, *J.Virol.*, 1991, 65, 4887–4892.

What is claimed is:

1. A method for the preparation of (±)-calanolide A comprising steps of:

(a) reacting chromene 4 with paraldehyde in the presence of an acid catalyst to form chromanone 7; and (b) reducing chromanone 7 so as to form (±)-calanolide A.

2. The method of claim 1, wherein step (a) acid catalyst comprises trifluoroacetic acid, trifluoromethanesulfonic acid, methanesulfonic acid, or pyridinium salts thereof.

3. The method of claim 1, wherein step (b) is performed with a reducing agent comprising sodium borohydride, zinc borohydride, borane or selectrides in the presence of a metal additive comprising $CeCl_3(H_2O)_7$, $ZnCl_2$, $AlCl_3$, $TiCi_4$, $SnCl_3$, $LnCl_3$ or mixtures thereof with triphenylphosphine oxide.

4. 5-Hydroxy-2,2-dimethyl-6-(2-methyl-3-hydroxybutyro)-10-propyl-2H,8H-benzo[1,2-b:3,4-b') dipyran-8-one.

5. (−)-Calanolide A.

6. An anti-HIV composition which comprises an anti-HIV effective, non-toxic amount of (−)-calanolide A and a pharmaceutically acceptable carrier.

7. The composition of claim 6, which further comprises an antiviral effective amount of at least one additional antiviral compound.

8. The composition of claim 6, wherein said antiviral compound comprises AZT or DDC.

9. A method of preventing or treating an HIV infection in a mammal which comprises administering to a mammal an anti-HIV effective, non-toxic amount of (−)-calanolide A.

10. The method of claim 9, which further comprises co-administering an antiviral effective amount of at least one additional antiviral compound.

11. The method of claim 10, wherein said antiviral compound comprises AZT or DDC.

12. The method of claim 9, wherein the mammal is a human.

* * * * *